(12) United States Patent
Nagasawa et al.

(10) Patent No.: US 9,006,134 B2
(45) Date of Patent: Apr. 14, 2015

(54) PARTICULATE WATER ABSORBING AGENT AND MANUFACTURING METHOD OF SAME

(75) Inventors: Makoto Nagasawa, Nara (JP); Hiroyuki Ikeuchi, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 12/503,396

(22) Filed: Jul. 15, 2009

(65) Prior Publication Data
US 2009/0275470 A1   Nov. 5, 2009

Related U.S. Application Data

(63) Continuation of application No. PCT/JP2008/062041, filed on Jul. 3, 2008.

(30) Foreign Application Priority Data

Jul. 4, 2007 (JP) ................................. 2007-175787

(51) Int. Cl.

| | |
|---|---|
| *B01J 20/26* | (2006.01) |
| *B01J 20/02* | (2006.01) |
| *B01J 20/22* | (2006.01) |
| *C08F 20/06* | (2006.01) |
| *B01J 20/28* | (2006.01) |
| *A61F 13/53* | (2006.01) |

(Continued)

(52) U.S. Cl.
CPC ........... *B01J 20/28011* (2013.01); *A61F 13/53* (2013.01); *B01J 20/02* (2013.01); *B01J 20/26* (2013.01); *B01J 20/28004* (2013.01); *B01J 2220/46* (2013.01); *B01J 2220/68* (2013.01); *C08K 3/32* (2013.01); *C08K 5/175* (2013.01); *C08L 33/02* (2013.01)

(58) Field of Classification Search
USPC ........................ 502/400, 401, 402; 526/317.1
See application file for complete search history.

(56) References Cited

U.S. PATENT DOCUMENTS

| | | |
|---|---|---|
| 5,610,208 A | 3/1997 | Dairoku et al. |
| 6,444,744 B1 | 9/2002 | Fujimaru et al. |

(Continued)

FOREIGN PATENT DOCUMENTS

| | | |
|---|---|---|
| EP | 1466928 | 10/2004 |
| JP | 64-33158 | 2/1989 |

(Continued)

OTHER PUBLICATIONS

Chemicool.com, "Definition of amine." (c) 2013 Chemicool.com. Viewed Apr. 26, 2013 at http://www.chemicool.com/definition/amine.html.*

(Continued)

*Primary Examiner* — Stanley Silverman
*Assistant Examiner* — Daniel Berns
(74) *Attorney, Agent, or Firm* — Nixon & Vanderhye PC

(57) ABSTRACT

The application relates to the particulate water absorbing agent of the present invention composed primarily of a polyacrylic acid- or polyacrylate-based water absorbing resin and containing a chelating agent and a phosphorous compound. Accordingly, the particulate water absorbing agent composed primarily of a water absorbing resin achieves both excellent water absorbing properties and anti-coloring effect which would normally be incompatible. A particulate water absorbing agent for absorbent core is provided that is suitable for actual use.

10 Claims, 1 Drawing Sheet

(51) Int. Cl.
   *C08K 5/17* (2006.01)
   *C08K 3/32* (2006.01)
   *C08L 33/02* (2006.01)

(56) References Cited

U.S. PATENT DOCUMENTS

| | | |
|---|---|---|
| 7,098,284 B2 * | 8/2006 | Torii et al. .................. 526/317.1 |
| 2005/0013865 A1 | 1/2005 | Nestler et al. |
| 2005/0085604 A1 | 4/2005 | Handa et al. |
| 2007/0066167 A1 | 3/2007 | Wada et al. |
| 2007/0078231 A1 | 4/2007 | Shibata et al. |
| 2007/0123658 A1 | 5/2007 | Torii et al. |
| 2007/0141338 A1 | 6/2007 | Ishizaki et al. |

FOREIGN PATENT DOCUMENTS

| | | |
|---|---|---|
| JP | 4-331205 | 11/1992 |
| JP | 5-86251 | 4/1993 |
| JP | 2000-230129 | 8/2000 |
| JP | 2000-327926 | 11/2000 |
| JP | 2003-52742 | 2/2003 |
| JP | 2003-206381 | 7/2003 |
| JP | 2005-186016 | 7/2005 |
| WO | 00/55245 | 9/2000 |
| WO | 2005/012369 | 2/2005 |
| WO | 2005/027986 | 3/2005 |
| WO | 2005/092956 | 10/2005 |

OTHER PUBLICATIONS

Japanese Search Report mailed on Aug. 2, 2008 corresponding to PCT Application No. PCT/JP2008/062041 filed on Jul. 3, 2008.

International Preliminary Examination Report mailed on Aug. 2, 2008 corresponding to PCT Application No. PCT/JP2008/062041 filed on Jul. 3, 2008.

International Search Report mailed on Aug. 12, 2008 corresponding to PCT Application No. PCT/JP2008/062041 filed on Jul. 3, 2008.

Written Opinion of the International Searching Authority mailed on Aug. 12, 2008 corresponding to PCT Application No. PCT/JP2008/062041 filed on Jul. 3, 2008.

European Search Report for related European Application No. 08790834.9, five pages, mailed Apr. 4, 2012.

* cited by examiner

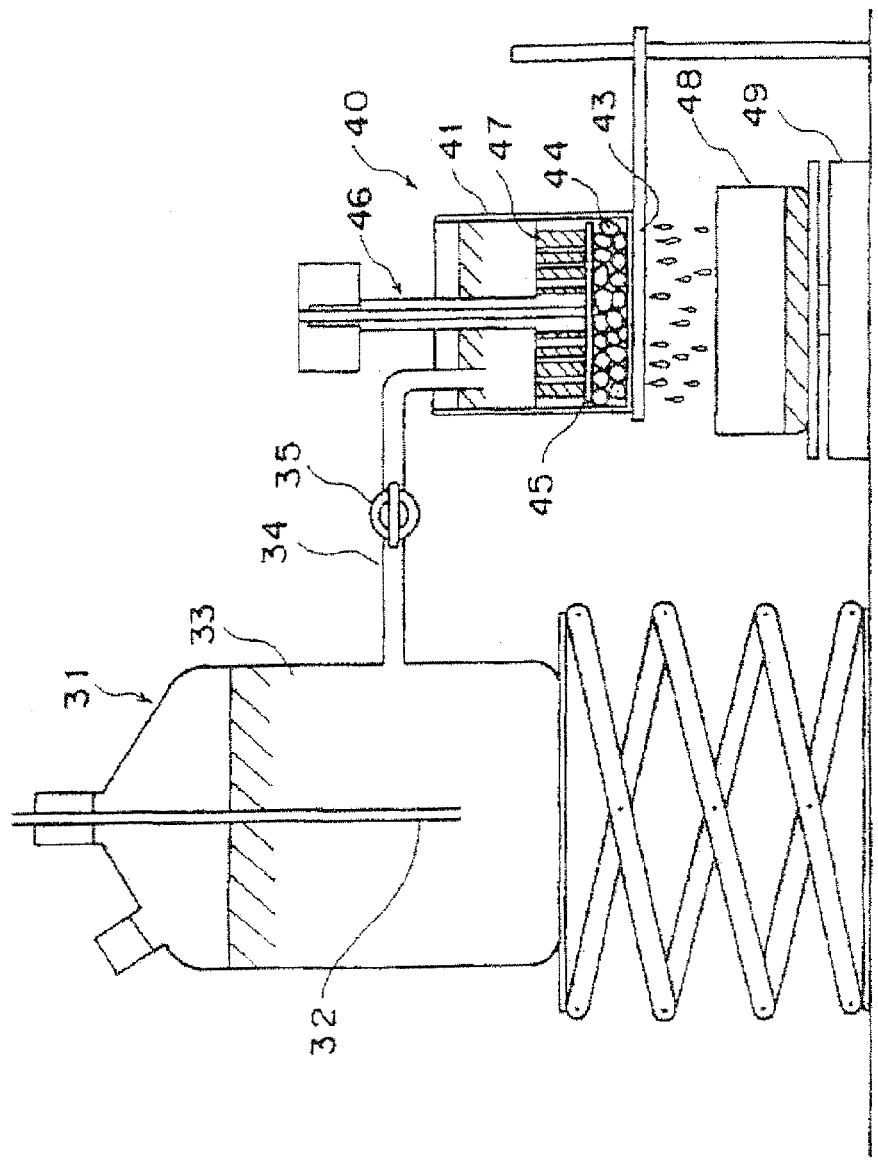

PARTICULATE WATER ABSORBING AGENT AND MANUFACTURING METHOD OF SAME

CROSS-REFERENCE TO RELATED APPLICATIONS

This application is a Continuation of PCT International Application Serial No. PCT/JP2008/062041 filed Jul. 3, 2008.

This application is based upon and claims the benefit of priority from prior Japanese Patent Application No. 2007-175787 filed Jul. 4, 2007.

TECHNICAL FIELD

The present invention relates to particulate water absorbing agents composed primarily of a polyacrylic acid- or polyacrylate-based water absorbing resin and manufacturing methods thereof. The present invention relates in particular to particulate water absorbing agents which are substantially white, exhibit an excellent urine resistance (gel degradation prevention property or gel stability), show no coloring over time, and possess high levels of physical properties and excellent safety, as well as manufacturing methods of such agents.

BACKGROUND ART

Highly water absorbing agents have been developed in recent years and used widely in disposable diapers, sanitary napkins, and like absorbing articles and also as water retaining agents for agriculture/horticulture and construction purposes, principally for disposable products. Raw materials, including various monomers and hydrophilic polymers, are being suggested for the manufactured of the water absorbing agent. Especially, polyacrylic acid- or polyacrylate-based water absorbing resins produced from an acrylic acid and/or a salt thereof as a monomer are the most popular for industrial uses for their excellent water absorbing capability.

Conventionally known, desirable water absorbing properties for the water absorbing agent include: centrifuge retention capacity, absorption capacity against pressure, water absorption rate, liquid permeability under no load, liquid permeability under load, shock resistance, urine resistance, fluidity, gel strength, particle size, and many other properties (parameters). In addition, various definitions (parameter measuring methods) are being suggested for the same physical property (e.g., centrifuge retention capacity) from various viewpoints.

Since the water absorbing agent is used principally for diapers, sanitary napkins, and other sanitary articles, if the water absorbing agent in powder form is actually used with white pulp in a sanitary article, the water absorbing resin is required to be white upon shipment from a factory in order to avoid giving consumers an uncomfortable feeling due to coloring. A water absorbing agent is typically white powder. It is known however that the agent will color over time (change from yellow to brown) after shipment, during storage and transport and also when used in sanitary articles. Hence, the absorbing articles are required to remain white after being stored for an extended period of time. The coloring problems are increasingly challenging due to the recent trend of rising usage (wt %) of water absorbing resin in sanitary articles.

There is a large literature addressing the coloring problems of the water absorbing agent. Patent document 1 suggests a method of polymerizing an acrylic acid and/or a salt thereof using hydroxy peroxide and a reducing agent and thereafter processing the product with a silane coupling agent. Patent document 2 suggests a method of processing a water absorbing resin with an organic phosphorous compound or a salt thereof. Patent document 3 suggests a method of controlling the total amount of hydroquinone and benzoquinone in an acrylic acid to or below 0.2 ppm. Patent document 4 suggests a method of adding an inorganic reducing agent to a water absorbing resin. Patent documents 5, 6, 7 suggest a method of adding an organic carboxylic acid or a salt thereof to a water absorbing resin. Patent document 8 suggests a manufacturing method of polymerizing an acrylic acid containing tocopherol as a polymerization inhibitor. Patent documents 9, 10, 11 suggest a manufacturing method of adding a metal chelating agent in the manufacture of a water absorbing resin. Patent document 12 suggests a manufacturing method of adding acid in the manufacture of a water absorbing resin.

All these methods degrade physical properties and lead to additional cost, without providing sufficient improvements in the coloring problems. Also, some compounds used could be hazardous.

Patent document 1: Japanese Unexamined Patent Publication No. 4-331205/1992 (Tokukaihei 4-331205)

Patent document 2: Japanese Unexamined Patent Publication No. 5-86251/1993 (Tokukaihei 5-86251)

Patent document 3: U.S. Pat. No. 6,444,744

Patent document 4: International Patent Application Published under the PCT, No. WO2000/55245

Patent document 5: Japanese Unexamined Patent Publication (Tokukai) No. 2000-327926

Patent document 6: Japanese Unexamined Patent Publication (Tokukai) No. 2003-52742

Patent document 7: Japanese Unexamined Patent Publication (Tokukai) No. 2005-186016

Patent document 8: International Patent Application Published under the PCT, No. WO2003/53482

Patent document 9: Japanese Unexamined Patent Publication (Tokukai) No. 2003-206305

Patent document 10: Japanese Unexamined Patent Publication (Tokukai) No. 2003-206381

Patent document 11: U.S. Pat. No. 5,610,208

Patent document 12: International Patent Application Published under the PCT, No. WO2005/92956

DISCLOSURE OF INVENTION

The invention has an objective to achieve, in a particulate water absorbing agent composed primarily of a water absorbing resin, both excellent water absorbing properties and anti-coloring effect which are normally incompatible.

The present invention provides a particulate water absorbing agent, containing a chelating agent and a phosphorous compound, which is composed primarily of a polyacrylic acid- or polyacrylate-based water absorbing resin.

Additional objects, advantages and novel features of the invention will be set forth in part in the description which follows, and in part will become apparent to those skilled in the art upon examination of the following or may be learned by practice of the invention.

BRIEF DESCRIPTION OF DRAWINGS

FIG. 1 is a schematic of a device used to measure 0.69 mass % saline flow conductivity (SFC).

REFERENCE NUMERALS

31 . . . Tank
32 . . . Glass Tube

33 . . . 0.69 mass % Aqueous Solution of Sodium Chloride
34 . . . L-shaped Tube with Faucet
35 . . . Faucet
40 . . . Container
41 . . . Cell
43 . . . Stainless Steel Net
44 . . . Swollen Gel
45 . . . Glass Filter
46 . . . Piston
47 . . . Holes Through Piston
48 . . . Collecting Vessel
49 . . . Pan Scales

BEST MODE FOR CARRYING OUT INVENTION

The following will describe the present invention in more detail.
(1) Particulate Water Absorbing Agent The particulate water absorbing agent of the present invention invariably contains a chelating agent and a phosphorous compound (detailed later) and preferably further containing a polyvalent metal salt, an inorganic powder, etc., the components preferably being integrated with a water absorbing resin.

In the present invention, the "particulate water absorbing agent" refers to an agent that solidifies when absorbing an aqueous liquid composed primarily of a water absorbing resin (also termed: gellant). The aqueous liquid is by no means limited to water; it could be urine, blood, faeces, a waste liquid, moisture, vapor, ice, a mixture of water and an organic or inorganic solvent, rain water, or ground water, and any other substance that contains water. Preferably, the particulate water absorbing agent of the present invention is an agent that solidifies when absorbing urine, especially human urine.

The primarily component (water absorbing resin) of the particulate water absorbing agent of the present invention accounts for preferably 70 to 99.9 mass %, more preferably 80 to 99.7 mass %, and even more preferably 90 to 99.5 mass %, of the entire particulate water absorbing agent.

The chelating agent, an essential component of the particulate water absorbing agent of the present invention, is preferably soluble in water. The chelating agent accounts for preferably 10 to 5,000 mass ppm, more preferably 10 to 1,000 mass ppm, even more preferably 50 to 1,000 mass ppm, still more preferably 100 to 1,000 mass ppm, of the particulate water absorbing agent of the present invention. Specifying a value outside these ranges is not preferable. Below those figures, desired urine resistance and anti-coloring effect (over time or not over time) become unavailable. Beyond the ranges, polymerization reactions become difficult to control, especially when the chelating agent is added and mixed with an unsaturated monomer to polymerize an aqueous solution of the unsaturated monomer.

The phosphorous compound, an essential component of the particulate water absorbing agent of the present invention, is preferably soluble in water. The phosphorous compound accounts for preferably 0.01 to 3 mass %, more preferably 0.1 to 2 mass %, even more preferably 0.1 to 1 mass %, of the particulate water absorbing agent of the present invention. Specifying a value outside these ranges is not preferable. Below those figures, desired urine resistance and anti-coloring effect (over time or not over time) become unavailable. Beyond the ranges, absorbing properties (absorption capacity, water-soluble content), liquid permeability, and surface tension, among others, deteriorate, especially when the phosphorous compound is added to the water absorbing resin.

An anti-coloring agent, such as a reducing agent or an antioxidant, may be added in a rate of 0 to 2 wt %, preferably 0.001 to 1 mass %.

The raw materials (unsaturated monomer, chelating agent, phosphorous compound, polyvalent metal salt, etc.) for the water absorbing agent are preferably soluble in water. Throughout the following description, as far as the present invention is concerned, compounds which have a solubility of at least 1 g or greater, preferably 5 g or greater, more preferably 10 g or greater, in 100-mL ion exchange water at $25\pm2°$ C. at normal pressure are regarded as being water-soluble.
(2) Water Absorbing Resin In the present invention, the "water absorbing resin" refers to a water-swelling, water-insoluble polymer, a polymer into which is introduced a crosslinked structure. A substance is regarded as being water-swelling if it has a centrifuge retention capacity (CRC) of 2 g/g or greater, preferably 5 to 200 g/g, more preferably 20 to 100 g/g, in physiological saline. A resin is regarded as being (practically) water-insoluble if its extractable polymer content accounts for 0 to 50 mass % and never greater, preferably 0 to 25 mass %, more preferably 0 to 15 mass %, even more preferably 0 to 10 mass %, of the resin. These properties are measured by the methods defined later in examples of the invention.

The water absorbing resin for use in the present invention is a polyacrylic acid- or polyacrylate-based water absorbing resin containing 10 to 100 mol %, preferably 50 to 100 mol %, more preferably 70 to 100 mol %, and even more preferably 90 to 100 mol % acrylic acid (acrylate) in structural repeat units, because such a resin delivers desirable physical properties and anti-coloring effect.

The polyacrylic acid (acrylate) has some of its acid groups preferably being neutralized to achieve desirable physical properties. The neutralization ratio of the acid groups is preferably 10 to 99 mol %, more preferably 20 to 99 mol %, more preferably 40 to 95 mol %, even more preferably 50 to 90 mol %, still more preferably 50 to 80 mol %, and most preferably 60 to 75 mol %. The acid groups are neutralized by alkali metal salt (e.g. lithium, sodium, potassium) or a monovalent salt of acrylic acid (e.g. ammonium salt, amine salt), preferably by an alkali metal salt. The neutralization may be performed on the monomer before polymerization or on the polymer during or after polymerization. A combination of these methods is an examples. Preferably, the acrylic acid as a monomer is neutralized in view of uniformity.

A water absorbing resin other than the polyacrylic acid- or polyacrylate-based water absorbing resin may be used along with the polyacrylic acid- or polyacrylate-based water absorbing resin in the present invention. In any case, preferably, the polyacrylic acid- or polyacrylate-based water absorbing resin(s) is/are the primary component(s). Specifically, the polyacrylic acid- or polyacrylate-based water absorbing resin(s) account(s) for preferably 50 to 100 mass %, more preferably 70 to 100 mass %, and even more preferably 90 to 100 mass % of the total water absorbing resin(s). The other water absorbing resin is, for example, a polyamine-based water absorbing resin (a crosslinked polymer of polyethyleneimine, polyallylamine, etc.) or a non-ionic water absorbing resin (a crosslinked polymer of polyacrylamide, polyethylene oxide, etc.). In the present invention, mixtures of the polyacrylic acid- or polyacrylate-based water absorbing resin(s) and any of these other water absorbing resins are regarded as polyacrylic acid- or polyacrylate-based water absorbing resins.

(3) Chelating Agent (Preferably, Water-soluble Organic Chelating Agent)

A chelating agent is always used in the present invention. The chelating agent is preferably a water-soluble organic chelating agent, more preferably a non-polymer compound organic chelating agent containing a nitrogen atom and/or a phosphor atom, even more preferably any compound selected from the group consisting of amino polyvalent carboxylic acid, organic polyvalent phosphoric acid, and amino polyvalent phosphoric acid, in view of effect.

The chelating agent used in the present invention is a compound that catches transition metal ions and/or other metal ions. The chelating agent is preferably a non-polymer compound organic chelating agent with a weight-average molecular weight of 5,000 or less, more preferably a non-polymer compound organic chelating agent with a molecular weight of 100 to 1,000, in view of influence on the polymerization and the physical properties of the water absorbing agent obtained. If the molecular weight is in excess of 5,000, the unsaturated monomer could show a high viscosity when mixed with an aqueous solution, making it difficult to control polymerization temperature, depending on the polymerization method. This is not preferable.

Among non-polymer compound organic chelating agents, those compounds which contain a nitrogen atom and/or a phosphor atom are preferred. Amino polyvalent carboxylic acid (salt) with two, three, or more carboxyl or phosphate groups in each molecule and an organic phosphoric acid (salt) compound with phosphorous groups are preferred. The amino polyvalent carboxylic acid (salt) has more preferably 3 to 100, even more preferably 3 to 20, and still more preferably 3 to 10 carboxyl groups in each molecule.

Examples of the amino polyvalent carboxylic acid (salt) with two or more carboxyl groups include amino carboxylic acid/metal chelating agents, such as iminodiacetic acid, hydroxyethyl iminodiacetic acid, nitrilotriacetic acid, nitrilotripropionic acid, ethylenediaminetetraacetic acid, hydroxyethylenediaminetriacetic acid, hexamethylenediaminetetraacetic acid, diethylenetriaminepentacetic acid, triethylenetetraminehexaacetic acid, trans-1,2-diaminocyclohexanetetraacetic acid, bis(2-hydroxyethyl)glycine, diaminopropanoltetraacetic acid, ethylenediamine-2-propionic acid, glycol ether diaminetetraacetic acid, bis(2-hydroxy benzyl)ethylenediaminediacetic acid, ethylenediamine disuccinic acid, L-glutamic diacetic acid, 3-hydroxy-2,2'-iminodisuccinic acid, glycol ether diaminetetraacetic acid, methylglycine diacetic acid, and salts of these substances. Any one, two, or more of them may be used.

The organic phosphorous compound is, for example, hydroxyethylene diphosphoric acid containing two phosphorous groups per molecule. More preferable examples include organic polyvalent phosphorous compounds containing three or more phosphorous groups per molecule and amino polyvalent phosphorous compounds containing amino groups.

Examples of organic polyvalent phosphorous compounds containing three or more phosphorous groups per molecule and amino polyvalent organic phosphorous compounds include ethylenediamine-N,N'-di(methylene phosphinic acid), ethylenediamine tetra(methylene phosphinic acid), nitriloacetic-di(methylene phosphinic acid), nitrilodiacetic-(methylene phosphinic acid), nitriloacetic-β-propionic-methylene phosphonic acid, nitrilotris(methylene phosphonic acid), cyclohexanediamine tetra(methylene phosphonic acid), ethylenediamine-N,N'-diacetic-N,N'-di(methylene phosphonic acid), ethylenediamine-N,N'-di(methylene phosphonic acid), ethylenediamine tetra(methylene phosphonic acid), polymethylenediamine tetra(methylene phosphonic acid), diethylenetriamine penta(methylene phosphonic acid), 1-hydroxy ethylidene diphosphonic acid, and salts of these substances.

Any one, two, or more of the amino carboxylic acids (salts) with three or more carboxyl groups and the organic phosphoric acids (salts) may be used together. Preferable salts include alkali metal salts, such as sodium salt and potassium salt, ammonium salts, and amine salts, in view of solubility in water.

The most preferable chelating agent of these is an amino polyvalent organic phosphorous compound which contains an amino phosphonic group in view of water absorbing capabilities (absorption capacity, saline flow conductivity (SFC), anti-gel degradation prevention property, and coloring prevention) with respect to the amount of chelating agent added.

As an example of a preferred manufacturing method for the particulate water absorbing agent of the present invention, the chelating agent is preferably added to an unsaturated monomer (detailed later), to achieve prominent effects from the present invention.

(4) Phosphorous Compound (Preferably, Water-soluble Inorganic Phosphorous Compound)

The phosphorous compound in the particulate water absorbing agent of the present invention may be either organic or inorganic, and preferably water-soluble. If the phosphorous compound is water-insoluble, the phosphorous compound shows poor affinity with the water-containing gel-like polymer and the water absorbing resin obtained in the step mentioned earlier. The poor affinity in turn mitigates the anti-coloring effect, whether over time or not, of the particulate water absorbing agent, which is the objective of the present application. This is not desirable.

The phosphorous compound of the present invention is preferably inorganic in view of prevention of deterioration of physical properties (absorption capacity under load, especially, surface tension) of the water absorbing agent obtained.

If a particulate water absorbing agent to which is added a compound that induces a falling surface tension is used, for example, as the absorbent core of disposable diapers, urine may under pressure flow back again from the absorbent core before the urine is absorbed by the particulate water absorbing agent. That causes the user feel uncomfortable and hence is not desirable.

An especially preferable phosphorous compound in the present invention is a water-soluble inorganic phosphorous compound. Specific examples include phosphoric acid, phosphorous acid, hypophosphorous acid, triphosphoric acid, tripolyphosphoric acid, and salts of these substances (for example, disodium hydrogenphosphate, sodium dihydrogenphosphate, and trisodium phosphate). An especially preferable compound is phosphoric acid (or its salt) in view of absorbing properties of the water absorbing agent because the acid/salt is not reducing. Any one of the water-soluble inorganic phosphorous compounds may be used alone. Alternatively, two or more of the water-soluble inorganic phosphorous compounds may be used together. Preferable salts include water-soluble monovalent salts: namely alkali metal salts, such as sodium salt and potassium salt, ammonium salt, and amine salt. Among these salts, the most preferred is acidic with pH 7 or lower in view of temporal coloring prevention effect: namely, phosphoric acid, sodium dihydrogenphosphate, potassium dihydrogenphosphate, and ammonium dihydrogenphosphate.

As an example of a preferred manufacturing method for the particulate water absorbing agent of the present invention, the phosphorous compound(s) is/are added after the polymerization, for example, preferably to the water-containing gel-like polymer after the polymerization, a dry pulverized product after the drying, the water absorbing resin before or after the surface crosslinking, and the water absorbing resin before or after the surface treatment with the polyvalent metal, especially preferably simultaneously with or after the surface crosslinking of the water absorbing resin, before or simultaneously with the surface treatment with the polyvalent metal salt, to achieve the effects of the invention. Furthermore, to achieve the effects of the invention more prominently, most preferably, the phosphorous compound(s) is/are added after the surface crosslinking of the water absorbing resin or before the surface treatment with the polyvalent metal salt.

The addition of the preferred phosphorous compound(s) prominently achieve(s) the effects of the invention because the addition prevents, for example, metal ions contained in urine or another absorbed liquid that permeates the particulate water absorbing agent from the outside from diffusing into particles, for example, when the agent is actually used in sanitary articles. Therefore, the phosphorous compound(s) preferably exist on the surface or near the surface layer of the particulate water absorbing agent without binding with the polymers which constitute crosslinks, for example, in such a state that the compound(s) can be extracted from the particulate water absorbing agent in an aqueous liquid, such as water or an aqueous solution of a hydrophilic organic solvent.

Furthermore, the presence of a free phosphorous compound on the surface or near the surface layer of the particulate water absorbing agent prevents, for example, other additives and polyvalent metal salts added where necessary from diffusing into particles, hence achieving the effects of the invention more prominently.

If the phosphorous compound(s) is/are added before or during the polymerization, for example, to the unsaturated aqueous solution of a monomer (discussed later), the phosphorous compound(s) bind(s) with the crosslinked polymer of the water absorbing resin, which is the major component of the particulate water absorbing agent, because the polymerization becomes difficult to control and the phosphorous compound(s) (especially, reducing phosphorous compound(s), such as hypophosphorous acid (salt)) causes, for example, chain transfer reactions. That hugely degrades the effect of preventing, for example, the metal ions contained in a liquid that permeates the particulate water absorbing agent from the outside from diffusing into particles. That is undesirable. Water absorbing agents are not obtained which have the water absorbing capabilities of the present invention (absorption capacity, saline flow conductivity (SFC), anti-gel degradation prevention property, and coloring prevention).

(5) Method of Manufacturing Particulate Water Absorbing Agent

An example of the method of manufacturing the particulate water absorbing agent of the present invention is a method of manufacturing a particulate water absorbing agent composed primarily of a polyacrylic acid- or polyacrylate-based water absorbing resin and involves a step of crosslinking/polymerizing an aqueous solution of a monomer composed primarily of acrylic acid (acrylate) and step of drying the water-containing gel-like polymer obtained by the polymerization, wherein a chelating agent and a phosphorous compound are added in the steps of manufacturing the following water absorbing resin.

The chelating agent and the phosphorous compound may be added by, for example, one of or any combination of water absorbing resin manufacturing steps (A) to (F) below.

Step (A): Preparing an aqueous solution of a monomer composed primarily of acrylic acid (acrylate).

Step (B): Adding a polymerization initiator to the aqueous solution of a monomer prepared in step (A) or shining an ultraviolet or similar activation energy beam onto the aqueous solution of a monomer prepared in step (A) to crosslink/polymerize the monomer in the solution.

Step (C): After the crosslinking/polymerization of the monomer in the solution, crushing the water-containing gel-like polymer obtained by the polymerization and neutralizing simultaneously with or after the crushing where necessary.

Step (D): After steps (A) to (C), drying the water-containing gel-like polymer and pulverizing the polymer where necessary to obtain dry powder which contains 0 to 5 mass % 150-μm or smaller particles, has a mass-average particle diameter (D50) of 200 to 600 μm, and has a particle size distribution of which the logarithmic standard deviation (σζ) is 0.20 to 0.40.

Step (E): Crosslinking the surface of the dry powder obtained in step (D) with a surface crosslinking agent to obtain a water absorbing resin.

Step (F): After the surface crosslinking, processing the surface further with a polyvalent metal salt where necessary, to obtain a water absorbing resin. The step of adding a polyvalent metal salt in the manufacture of the water absorbing resin is referred to as the "polyvalent metal salt adding step" throughout the specification.

To achieve the effects of the present invention, a manufacturing method is preferred which involves, among the manufacturing methods, a step of polymerizing an aqueous solution of a monomer composed primarily of acrylic acid (acrylate) and a step of drying the water-containing gel-like crosslinked polymer obtained by the polymerization and in which a step of adding a chelating agent and a step of adding a phosphorous compound are carried out sequentially.

"[A] step of adding a chelating agent and a step of adding a phosphorous compound are carried out sequentially" means adding a phosphorous compound after a chelating agent is added in the manufacture of the water absorbing resin. In other words, a chelating agent is added in any of, for example, steps (A) to (F) as representative manufacturing steps for the water absorbing resin, and a phosphorous compound is further added in a later step. In the manufacturing steps for the water absorbing resin of the present invention, the polymerization and drying steps are essential, whereas steps (A) are (F) not. There may be any other steps, such as deaeration, granulation, and addition of a modifier.

Preferably in the manufacturing method of the present invention, the chelating agent is added to an aqueous solution of a monomer before the drying, more preferably during the polymerization or being polymerized. The phosphorous compound is added to the polymerized water-containing gel-like crosslinked polymer or the dry powder thereof. More preferably, the phosphorous compound is added during or after the drying, especially preferably after the drying, more preferably simultaneously with or after the surface crosslinking. In other words, the chelating agent is typically added in steps (A) to (C) before the drying, and the phosphorous compound is preferably added in steps (D) to (F) during or after the drying, more preferably in steps (E) to (F) after the drying. The phosphorous compound preferably resides on the surface or in a layer close to the surface of water absorbing resin particles especially in view of prevention of coloring and gel degradation. The phosphorous compound is therefore added during or after the drying, more preferably in one of the preferred steps after the drying.

These chelating agent and phosphorous compound may be added to the water absorbing agent without using a solvent. If the agent and compound are added in solid form, they may be added in the form of a powder mixture (dry blend). For better fixing the chelating agent and the phosphorous compound to the water absorbing agent, however, the agent and compound are added in the form of a solution, preferably in the form of an aqueous solution or an aqueous liquid. The solvent is water or a mix solvent of an organic solvent and water. That water or mix solvent accounts for 0.01 to 10 parts by mass, preferably 0.05 to 30 parts by mass, more preferably 0.1 to 10 parts by mass of 100 parts by mass water absorbing resin. The concentration of the aqueous solution is about 1 to 50 mass %. If necessary, a surfactant and other substances may be used. The solvent is dried out where necessary.

(6) Place of Existence of Chelating Agent and Phosphorous Compound

These chelating agents, in the present invention, need to be integrated into the particulate water absorbing agent (water absorbing resin) and reside on the surface of the water absorbing resin or inside the water absorbing resin. The chelating agents preferably reside inside the water absorbing resin for better urine resistance (anti-gel degradation effect) and coloring prevention.

The phosphorous compound needs to be integrated into the particulate water absorbing agent (water absorbing resin) and resides locally on the surface or in a layer close to the surface of water absorbing resin particles. The phosphorous compound preferably resides on the surface of the water absorbing resin for better coloring prevention.

The following will further describe methods of manufacturing the water absorbing resin and the particulate water absorbing agent according to the present invention.

(7) Acrylic Acid

An acrylic acid and/or a salt thereof is used in 10 to 100 mol % as an unsaturated monomer in the present invention. See the description in item (2) for a range of the amount of acrylic acid used, a range of the neutralization ratio, and specific types of the acrylic acid.

The acrylic acid preferably contains a particular amount of polymerization inhibitor. The polymerization inhibitor is preferably a methoxy phenol, more preferably p-methoxy phenol. The proportion of the methoxy phenol to the acrylic acid is 10 to 200 mass ppm, preferably 10 to 90 mass ppm, more preferably 20 to 90 mass ppm.

The acrylic acid of the present invention contains preferably as little protoanemonin and/or furfural (impurities) as possible, more preferably as little as 0 to 20 mass ppm. The protoanemonin and/or furfural content in the acrylic acid is more preferably 0 to 10 mass ppm, more preferably 0.01 to 5 mass ppm, even more preferably 0.05 to 2 mass ppm, still more preferably 0.1 to 1 mass ppm.

(8) Other Unsaturated Monomer(s)

One or more other unsaturated monomers may be used if necessary. The monomer(s) use along with the acrylic acid is/are, for example, the monomers recited in the U.S. and European patents listed later. Specific examples include methacrylic acid, maleic anhydride, fumaric acid, crotonic acid, itaconic acid, vinyl sulfonic acid, 2-(meth)acrylamide-2-methylpropanesulfonic acid, and (meth)acryloxyalkane-sulfonic acid, and alkali metal salts and ammonium salts thereof; and N-vinyl-2-pyrrolidone, N-vinyl acetoamide, (meth)acrylamide, N-isopropyl(meth)acrylamide, N,N-dimethyl(meth)acrylamide, 2-hydroxyethyl(meth)acrylate, methoxypolyethylene glycol (meth)acrylate, polyethylene glycol (meth)acrylate, isobutylene, lauryl(meth)acrylate, and other substances containing a water-soluble or hydrophobic unsaturated monomer as a copolymerizable component.

(9) Internal Crosslinking Agent

The crosslinking method employed in the present invention is by no means restricted in a special manner. Examples include crosslinking after adding a crosslinking agent during or after the polymerization, radical crosslinking using a radical polymerization initiator, and crosslinking using an electron beam or like radioactive beam. Preferably, a predetermined amount of internal crosslinking agent is added to the monomer for polymerization, and crosslinking reactions take place at the same tine or after the polymerization.

The proportion of the internal crosslinking agent used to the unsaturated monomer is determined to a suitable value from 0 to 3 mol %, preferably from 0.0001 to 2 mol %, more preferably from 0.005 to 1.5 mol %, even more preferably from 0.01 to 1.0 mol %, in view of physical properties.

Examples of the internal crosslinking agent used in the present invention include polymerizable internal crosslinking agents, such as N,N'-methylene bisacrylamide, (poly)ethylene glycol di(meth)acrylate, (poly)propylene glycol di(meth)acrylate, (polyoxyethylene) trimethylolpropane tri(meth)acrylate, trimethylolpropane di(meth)acrylate, or poly(meth)allyloxyalkane; and internal crosslinking agents which react with carboxyl groups, such as polyglycidyl ether (e.g. ethylene glycol diglycidyl ether), polyol (e.g. ethylene glycol, polyethylene glycol, glycerine, or sorbitol), and alkylene carbonate (e.g. ethylene carbonate). Any one, two, or more of these examples may be used.

If an internal crosslinking agent(s) is/are used, a polymerizable internal crosslinking agent is preferably used for better water absorbing properties of the water absorbing agent.

(10) Preparation of Aqueous Solution of Unsaturated Monomer (Step A)

If the polymerization step is implemented by reverse suspension polymerization, aqueous polymerization, etc., the unsaturated monomer is used, where necessary, in the form of an aqueous solution containing the internal crosslinking agent. The concentration of the unsaturated monomer content in the aqueous solution (hereinafter, the "aqueous monomer solution) is preferably 10 to 70 mass %, more preferably 15 to 65 mass %, even more preferably 30 to 65 mass %, still more preferably 30 to 60 mass %, most preferably 35 to 55 mass %, in view of physical properties. A solvent other than water may be used together where necessary. The type of the solvent used together is not limited in any particular manner.

Especially, if the chelating agent is mixed with the aqueous monomer solution as a preferred example of the manufacturing method in accordance with the present invention, the chelating agent may be mixed in any manner. Preferably, however, the chelating agent is added and mixed with the monomer or the aqueous monomer solution to prepare an aqueous solution of an unsaturated monomer.

The physical properties of the water absorbing resin and the water absorbing agent may be improved by adding, to the monomer, a water-soluble or water absorbing resin, such as polyvinyl alcohol, starch, or polyacrylic acid (acrylate), for example, in 0 to 50 mass %, preferably 0 to 20 mass %, and also adding various foaming agents (carbonate, azo compound, air bubbles, etc.), surfactants, and additives (detailed later), for example, in 0 to 5 mass %, preferably 0 to 1 mass %, upon the polymerization.

(11) Polymerization Step (Step B)

The aqueous solution of an unsaturated monomer is polymerized by ordinary, aqueous polymerization or reverse suspension polymerization for better performance and ease in the control of the polymerization. Although implementable in an air atmosphere, these polymerization methods are preferably carried out in a nitrogen, argon, or other inactive gas atmosphere (for example, 1% or less oxygen). The monomer content is used for polymerization after the oxygen dissolved is sufficiently replaced by the inactive gas (for example, 1 ppm or less oxygen). In the present invention, continuous belt polymerization and continuous or batch kneader polymerization are taken as especially preferred aqueous polymerization that is especially suitable to aqueous polymerization which boasts high productivity and delivers good physical properties, but in which the control of the polymerization is difficult.

Reverse suspension polymerization is a polymerization method in which the aqueous monomer solution is suspended in a hydrophobic organic solvent and described in, for example, U.S. Pat. Nos. 4,093,776, 4,367,323, 4,446,261, 4,683,274, and 5,244,735. Aqueous polymerization is a method in which the aqueous monomer solution is polymerized without using a dispersion solvent and described in, for example, U.S. Pat. Nos. 4,625,001, 4,873,299, 4,286,082, 4,973,632, 4,985,518, 5,124,416, 5,250,640, 5,264,495, 5,145,906, and 5,380,808 and European Patents Nos. 0811636, 0955086, 0922717, and 1178059. The monomers, crosslinking agents, polymerization initiators, and various other additives described in these patents can also be used in the present invention.

The interval from the preparation of the monomer content and/or the neutralization of the acrylic acid to the start of the polymerization of the monomer is preferably as short as possible in the present invention to improve absorbing properties and prevent coloring (yellowing), which are objectives of the present invention. The interval is preferably not longer than 24 hours, more preferably not more than 12 hours, even more preferably not more than 3 hours, still more preferably not more than 1 hour. The neutralization and preparation of the monomer content, in industry, are carried out in tanks in large quantities. Therefore, the interval often exceeds 24 hours. This is undesirable because the longer the interval from the preparation of the monomer content and/or the neutralization of the acrylic acid, the more the residual monomer and the more the water absorbing resin yellows. Thus, to reduce the interval, continuous neutralization and continuous monomer content preparation are preferably implemented, which is followed by batch polymerization or continuous polymerization. More preferably, continuous polymerization is implemented.

Examples of the polymerization initiator used in the polymerization of the aqueous monomer solution include persulfuric acid salt, such as potassium persulfate, ammonium persulfate, and sodium persulfate; t-butylhydroperoxide; hydrogen peroxide; 2,2'-azobis(2-amidino propane) dihydrochloride, 2-hydroxy-1-phenyl-propan-1-one, and benzoin methyl ether. In addition, a reducing agent, such as L-ascorbic acid, which accelerates dissociation of these polymerization initiators is used together. Furthermore, combinations of these initiators and reducing agents, that is, redox initiators, may be used. The initiators and redox initiators are used typically in 0.001 to 1 mol % or 0.001 to 0.5 mol % to the monomer.

Instead of using a polymerization initiator, the reaction system may be irradiated with a radioactive beam, electron beam, ultraviolet, or like activation energy beam to initiate polymerization reactions. Radioactive beam, electron beam, ultraviolet sensitization may be use together with a polymerization initiator.

The reaction temperature and reaction time of the polymerization is not limited in any particular manner and may be determined appropriately according to the type of the hydrophilic monomer and the polymerization initiator, reaction temperature, and other conditions. The reaction time is usually preferably not longer than 3 hours, more preferably not longer than 1 hours, even more preferably not longer than 0.5 hours, at the boiling point or lower temperatures. The peak temperature is preferably 150° C. or lower, more preferably 90 to 120° C. The water and acrylic acid that evaporate during the polymerization are preferably collected and recycled for manufacturing steps of the water absorbing resin where necessary.

As an example of a preferred manufacturing method for the particulate water absorbing agent of the present invention, the chelating agent is mixed with the aqueous monomer solution upon the polymerization. The "aqueous monomer solution upon the polymerization" is not limited to the aqueous monomer solution before the polymerization, but a concept encompassing the aqueous monomer solution during the polymerization and gel-like substances including that aqueous solution. The chelating agent is added at least once when the polymerization ratio of the monomer is 0 to 99 mol %, preferably 0 to 70 mol %, more preferably 0 to 50 mol %.

As an example of the manufacturing method, if the chelating agent is added to the aqueous monomer solution in the polymerization step, the chelating agent may be mixed either before or after introducing the polymerization initiator. The timing and method of the mixing are not limited in any particular manner. Preferably, however, the chelating agent is added to the aqueous monomer solution before the polymerization (polymerization ratio=0%).

(12) Water-containing Gel Crushing Step (Step C)

The water-containing gel-like crosslinked polymer obtained in the polymerization step implemented by aqueous polymerization (hereinafter, the "water-containing gel") may be dried as is. The polymer (gel) may however be crushed to powder form, for example, by using a gel crusher where necessary. The water-containing gel is maintained at, or heated to, preferably 40 to 95° C., more preferably 50 to 80° C. during the gel crushing in view of physical properties.

The resin solid content in the water-containing gel is not limited in any particular manner. The content is however preferably 10 to 70 mass %, more preferably 15 to 65 mass %, even more preferably 30 to 55 mass % in view of physical properties.

The gel crushing is carried out during or after the polymerization. Preferably, a continuous kneader is used. Alternatively, the gel may be extruded and thus crushed through a porous structure with pores measuring 0.3 to 20 mm, more preferably 0.5 to 10 mm, even more preferably 0.5 to 5.0 mm, across diameter. The pores are not limited in any particular manner in terms of their shape: for example, they may be circular, quadrangular (square, rectangular, etc.), triangular, or hexagonal. The pores are preferably circular. The diameter of a pore is defined by the diameter that is conceivable by regarding the outer boundary of an aperture as the circumference of a circle.

If the pores of the porous structure have a diameter smaller than 0.3 mm, the gel could be shaped like strings or cannot be extruded. If the pores of the porous structure have a diameter greater than 20 mm, the effects of the present invention may not be delivered.

Exemplary extrusion crushing devices are screw types, rotational roll types, and any other types that are capable of pressing the water-containing gel-like polymer all the way from their supply port through a porous plate. A screw-type extruder may have either one axis or plural axes. Those used in extrusion molding of edible meat, rubber, plastics, etc. or those used as crushers can be used in the invention. Examples include meat choppers and Dome Granulators®.

In that case, water, the polyvalent alcohols listed as examples of the internal crosslinking agent, the mix solutions of water and the polyvalent alcohols, the solutions obtained by dissolving the polyvalent metals listed as examples of the internal crosslinking agent in water, or vapor of these substances may be added.

As an example of a preferred manufacturing method for the particulate water absorbing agent of the present invention, the chelating agent is mixed during granulation (crushing) of the water-containing gel.

(13) Drying Step (Step D)

The water-containing gel-like crosslinked polymer obtained in the above step is dried further under particular temperature conditions to produce a dry product (or dry powder). The dry product is then pulverized, classified, and agglomerated as necessary, and surface crosslinked under particular temperature conditions.

The interval from the termination of the polymerization to the start of the drying (with an intervening gel crushing step if necessary) is preferably as short as possible to reduce the residual monomer and achieve gel degradation prevention (urine resistance) and yellowing prevention, which are objectives of the present invention. The water-containing gel-like crosslinked polymer obtained by the polymerization is subjected to drying (introduced into a drying device) starting within preferably 1 hour, more preferably 0.5 hours, even more preferably 0.1 hours after the termination of the polymerization. The temperature of the water-containing gel-like crosslinked polymer is controlled to preferably 50 to 80° C., more preferably 60 to 70° C., from the termination of the polymerization to the start of the drying to reduce the residual monomer and well mitigate coloring.

The polymerization, in industry, is carried out in large quantities. Therefore, the interval often exceeds 3 hours. This is undesirable because the longer the interval or the further the temperature goes out of the control range, the more the polymer is colored. Thus, continuous polymerization and continuous drying are preferred in order to reduce the interval.

The resin solid content, as calculated from reduction in mass by the drying (1 gram of powder or particles is heated at 180° C. for 3 hours) is regulated in the drying step to preferably 80 mass % or more, more preferably 85 to 99 mass %, even more preferably 90 to 98 mass %, still more preferably 92 to 97 mass % to obtain the dry product.

The drying temperature is not limited in any particular manner, but is preferably from 100 to 300° C., more preferably from 150 to 250° C. The water-containing gel-like crosslinked polymer may be dried by heating, in a heated air flow, by depressurization, infrared, micro waves, in a drum drier, by dehydration through azeotropy with the hydrophobic organic solvent, by high humidity drying using high temperature water vapor, and by various other methods. Preferably, the polymer is dried in a heated air flow of which the dew point is 40 to 100° C., more preferably 50 to 90° C. The drying may be carried out simultaneously with the polymerization in the present invention.

(14) Particle Size and Adjustment after Drying (Step D)

Particle size may be adjusted after the step of drying the water-containing gel-like crosslinked polymer or if necessary, after drying. Particle size is preferably adjusted to particular values to improve physical properties by surface crosslinking (detailed later). Particle size is adjustable by polymerization (especially, reverse suspension polymerization), pulverization, classification, agglomeration, collection of fine particles, etc.

The mass-average particle diameter (D50) before the surface crosslinking is adjusted to 200 to 600 μm, preferably 200 to 550 μm, more preferably 250 to 500 μm, even more preferably 300 to 450 μm, still more preferably 350 to 400 μm. There should be as few 150-μm or smaller particles as possible. After the adjustment, particles of that size account for usually 0 to 5 mass %, preferably 0 to 3 mass %, more preferably 0 to 1 mass %. There should be as few 850-μm or larger particles as possible. After the adjustment, particles of that size account for usually 0 to 5 mass %, preferably 0 to 3 mass %, more preferably 0 to 1 mass %. The logarithmic standard deviation ($\sigma\zeta$) of the particle size distribution is preferably 0.20 to 0.60, more preferably 0.27 to 0.50, even more preferably 0.25 to 0.45.

The steps described, for example, in U.S. Patent Application Publications Nos. 2004/181031 and 2004/2.42761 and U.S. Patent No. 2006/247351 may be used to adjust the particle size to predetermined particle size.

As an example of a preferred manufacturing method for the particulate water absorbing agent of the present invention, the phosphorous compound is added and mixed, before and after adjusting the particle size of the dry product, with the dry product adjusted in the drying step in terms of its resin solid content as described earlier.

(15) Surface Crosslinking Step (Step E)

Surface crosslinking of the water absorbing resin means increasing crosslinking density in at least parts of the surface layer (proximity of the surface: ordinary, from the surface down to the depth of a few tens of micrometers or less) of the water absorbing resin having a uniform crosslinked structure inside the polymer. A densely crosslinked layer may be formed by radical crosslinking of the surface or surface polymerization. Alternatively, the surface crosslinking may be carried out by crosslinking reactions with a surface crosslinking agent. The following will further describe the surface crosslinking using a surface crosslinking agent in the present invention where necessary.

The surface crosslinking agent used in the present invention may be various organic or inorganic crosslinking agents. The latter form crosslinks by ion bonding. In view of physical properties, a crosslinking agent which can react with carboxyl groups, especially an organic surface crosslinking agent which forms surface crosslinks by covalent bonding, is preferably used. Generally, a polyvalent alcohol compound, an epoxy compound, an oxetane compound, a polyvalent amine compound, a condensate of these compounds with a haloepoxy compound, an oxazoline compound, a monooxazolidinone compound, a dioxazolidinone compound, a polyoxazolidinone compound, an alkylene carbonate compound, etc. may be used.

Specific examples of the surface crosslinking agent used in the present invention are given in, for example, U.S. Pat. Nos. 6,228,930, 6,071,976, and 6,254,990 and include polyvalent alcohol compounds, such as monoethylene glycol, diethylene glycol, triethylene glycol, tetraethylene glycol, polyethylene glycol, monopropylene glycol, 1,3-propanediol, dipropylene glycol, 2,3,4-trimethyl-1,3-pentanediol, polypropylene glycol, glycerine, polyglycerine, 2-butene-1,4-diol, 1,4-butanediol, 1,3-butanediol, 1,5-pentanediol, 1,6-hexanediol, and 1,2-cyclohexane dimethanol; epoxy compounds, such as ethylene glycol diglycidyl ether and glycidol; polyvalent amine compounds, such as ethylenediamine, diethylenetriamine, triethylenetetramine, tetraethylenepentamine, pentaethylenehexamine, polyethyleneimine, and polyamide polyamine; haloepoxy compounds, such as epichlorohydrin, epibromohydrin, and α-methyl epichlorohydrin; condensates of these polyvalent amine compounds and haloepoxy compounds; oxazolidinone compounds, such as 2-oxazolidinone; and alkylene carbonate compounds, such as ethylene carbonate.

The surface crosslinking agent is however not limited in any particular manner. To maximum the effects of the present invention, at least a polyvalent alcohol, among these crosslinking agents, is preferably used. A polyvalent alcohol of carbon number 2 to 10, preferably of carbon number 3 to 8, is used.

The amount of surface crosslinking agent used, although variable depending on the compound used, the combination of compounds used, and other factors, is preferably 0.001 parts by mass to 10 parts by mass, more preferably 0.01 parts by mass to 5 parts by mass, relative to 100 parts by mass of the solid content in the resin. Water is preferably used in the surface crosslinking in the present invention. In that case, the amount of water used, although variable depending on the ratio of water content in the water absorbing resin used, is usually preferably 0.5 to 20 parts by mass, more preferably 0.5 to 10 parts by mass, relative to 100 parts by mass of the water absorbing resin.

A hydrophilic organic solvent may be used apart from water in the present invention. In that case, the amount the hydrophilic organic solvent used is usually preferably 0 to 10 parts by mass, more preferably 0 to 5 parts by mass, even more preferably 0 to 3 parts by mass, relative to 100 parts by mass of the water absorbing resin. The temperature of a solution of the crosslinking agent is preferably 0° C. to boiling point, more preferably 5 to 50° C., even more preferably 10 to 30° C., in view of ease in mixing and stability. The temperature of the water absorbing resin prior to mixing is preferably 0 to 800° C., more preferably 40 to 70° C., in view of ease in mixing. The additives described in U.S. Pat. Nos. 5,610,208 and 5,610,220 may be used.

Among various mixing methods, the following method is preferable in the present invention. Water and/or the hydrophilic organic solvent are mixed in advance where necessary. Next, that aqueous solution is either sprayed onto or mixed dropwise with the water absorbing resin. Spraying is preferred to dropwise addition. The size of sprayed droplets is preferably 1 to 300 μm, more preferably 10 to 200 μm, on average. A water-insoluble fine powder and a surfactant may be present together in the mixing in such a proportion that the effects of the present invention are not disrupted: for example, 0 to 10 mass %, preferably 0 to 5 mass %, more preferably 0 to 1 mass %. The surfactant used and its amount used are given, for example, in International Patent Application Published under the PCT, No. WO2005/75070 (International Patent Application Date: Feb. 4, 2005).

A preferred mixing device used in the mixing needs to thrust a large mix force to ensure uniform mixing. Various mixers may be used in the present invention: preferably a high speed stirring mixer, more preferably a high speed stirring continuous mixer. Specific examples include a Turbulizer (trade name of a product manufactured by Hosokawa Micron Corporation in Japan) and a Loedige mixer (trade name of a product manufactured by Loedige in Germany).

The water absorbing resin after being mixed with the surface crosslinking agent is preferably treated with heat. A condition in the heat treatment is preferably 120 to 250° C., more preferably 150 to 250° C. The duration of the heating is preferably from 1 minute to 2 hours. The heat treatment is usually carried out in a drying device or a heating furnace. The drying device is, for example, a groove-type mix drying device, a rotary drying device, a disc drying device, a flow layer drying device, an air flow drying device, and an infrared drying device. The water absorbing resin after the heating may be cooled down where necessary.

These surface crosslinking methods are described, for example, in European Patents Nos. 0349240, 0605150, 0450923, 0812873, 0450924, and 0668080, Japanese Unexamined Patent Publications Nos. 7-242709/1995 (Tokukaihei 7-242709) and 7-224304/1995 (Tokukaihei 7-224304), U.S. Pat. Nos. 5,409,771, 5,597,873, 5,385,983, 5,610,220, 5,633, 316, 5,674,633, and 5,462,972, and International Patent Applications Published under the PCT, Nos. WO99/42494, WO99/43720, and WO99/42496. These surface crosslinking methods are also applicable in the present invention.

As an example of a preferred manufacturing method for the particulate water absorbing agent of the present invention, the phosphorous compound is preferably added in the surface crosslinking step simultaneously with or after the surface crosslinking.

(16) Surface Treatment by Polyvalent Metal Salt (Step F)

The water absorbing resin of the present application delivers desired water absorbing properties, especially high liquid permeability (SFC), by surface treating the water absorbing resin with a polyvalent metal salt (also called "inorganic surface crosslinking agent"), that is, by crosslinking the water absorbing resin with a combination of a polyvalent metal salt and an organic surface crosslinking agent, especially by surface treating the water absorbing resin with a polyvalent metal salt after the surface crosslinking with an organic surface crosslinking agent.

The amount of the polyvalent metal salt used is 0 to 5 parts by weight, preferably 0.001 to 3 parts by weight, more preferably 0.01 to 2 parts by weight, relative to 100 parts by weight of the water absorbing resin.

The polyvalent metal salt used is a water-soluble polyvalent metal salt. Examples include aluminum chloride, aluminum polychloride, aluminum sulfate, aluminum nitrate, aluminum potassium sulfate, aluminum sodium sulfate, potassium alum, ammonium alum, sodium alum, sodium aluminate, calcium chloride, calcium nitrate, magnesium chloride, magnesium sulfate, magnesium nitrate, zinc chloride, zinc sulfate, zinc nitrate, zirconium chloride, zirconium, sulfate, and zirconium nitrate. A salt containing crystal water of these is preferably used in view of solubility in urine and other absorbed liquids.

Especially preferred among aluminum compounds are aluminum chloride, aluminum polychloride, aluminum sulfate, aluminum nitrate, aluminum potassium sulfate, aluminum sodium sulfate, potassium alum, ammonium alum, sodium alum, and sodium aluminate. Aluminum sulfate is especially preferable. Crystal hydrate powder, such as aluminum sulfate octadecahydrate, aluminum sulfate tetradecahydrate, aluminum sulfate pentadecahydrate, aluminum sulfate hexadecahydrate, aluminum sulfate heptadecahydrate, and aluminum sulfate octadecahydrate, can be most preferably used. Any one of them may be used alone. Alternatively, any two or more of these may be used together. The amount of used is the same as the ranges for the organic surface crosslinking agent mentioned earlier.

The polyvalent metal salt is preferably used in the form of solution, that is, dissolved in water, an aqueous liquid, and/or one of various hydrophilic organic solvents before use. An aqueous solution is the most preferable choice of the three. The optimal amount of, for example, an aqueous liquid added, which contains water and a hydrophilic organic solvent, may vary depending on the type of the water absorbing resin and particle size. The optimal amount of water is usually more than 0 parts by mass, up to 10 parts by mass or less, preferably 1 to 5 parts by mass, relative to 100 parts by mass of the solid content in the water absorbing resin. Similarly, the amount of the hydrophilic organic solvent used is usually more than 0 parts by mass, up to 10 parts by mass or less, preferably 0.1 to 5 parts by mass, relative to 100 parts by mass of the solid content in the water absorbing resin. The temperature of the solution is not limited in any particular manner and may be anywhere from the freezing point to the boiling point or 20° C. to 100° C. The solubility of the polyvalent metal salt may be adjusted according to temperature.

In the surface treatment using the polyvalent metal salt, the polyvalent metal salt is especially preferably added and mixed after the surface crosslinking using the organic surface crosslinking agent in view of water absorbing capability (especially, high liquid permeability), for surface treatment.

Surface treatments using a polyvalent metal salt and their conditions are described in International Patent Applications Published under the PCT, Nos. 2004/69915, 2004/113452, and 2005/108472. These surface treatments using a polyvalent metal salt is employed.

As an example of a preferred manufacturing method for the particulate water absorbing agent of the present invention, the phosphorous compound is preferably added in the surface crosslinking step before or simultaneously with the surface treatment using the polyvalent metal salt. The phosphorous compound is especially preferably added before the surface treatment using the polyvalent metal salt. Adding the phosphorous compound after the surface treatment using the polyvalent metal salt is not preferred because that degrades water absorbing properties.

In this specification, "the step of adding a polyvalent metal salt is involved after the step of adding a phosphorous compound" means that a polyvalent metal salt is further separately added after a phosphorous compound is added in the manufacture of a water absorbing resin.

(17) Surfactant

A surfactant may be added to the particulate water absorbing agent of the present invention where necessary to improve powder properties (powder fluidity, fluidity after absorbing moisture, etc.).

The amount of the surfactant used is preferably 0.1 to 1,000 mass ppm, more preferably 0.5 to 500 mass ppm, even more preferably 1 to 100 mass ppm, still more preferably 5 to 50 mass ppm, relative to the water absorbing resin. If the surfactant is used outside these ranges, desired powder fluidity effect may not be available, and absorbing properties may deteriorate.

Examples of the surfactant include anionic surfactants, such as fatty acid salts and higher alcohol sulfuric acid salts; polyoxyalkylene sorbitan fatty acid esters, such as polyoxyethylene sorbitan monolaurate, polyoxyethylene sorbitan monopalmitate, polyoxyethylene sorbitan monostearate, and polyoxyethylene sorbitan tristearate; alkyl amine salts, such as coconut amine acetate and stearylamine acetate; and other cationic surfactants and amphoteric surfactants. Apart from these examples, the surfactant described in U.S. Pat. No. 6,107,358 is applicable in the present invention.

The method of manufacturing the particulate water absorbing agent in accordance with the present invention may include a surfactant adding step. The surfactant adding step refers to the surfactant adding step in one of steps of manufacturing a particulate water absorbing agent or after all steps of manufacturing the particulate water absorbing agent. The surfactant is added in step (D), (E), or (F) or after (F), preferably in step (E) or (F) or after (F). In other words, the surfactant is preferably added simultaneously with the surface crosslinking step, simultaneously with the surface treatment using a polyvalent metal salt, or after the surface treatment using a polyvalent metal salt.

Therefore, a preferred method is, for example, surface crosslinking in a solution prepared by mixing a surface crosslinking agent, water (or hydrophilic organic solvent), and a surfactant. Another example is surface treatment in a solution prepared by mixing the polyvalent metal solution and a surfactant.

If no surfactant is added in the preferred method, desired powder properties may not be available.

(18) Particulate Water Absorbing Agent

In the present invention, a particulate water absorbing agent invariably contains a water absorbing resin, a chelating agent, and a phosphorous compound and if necessary, also contains an additive. The particulate water absorbing agent is preferably made by adding a phosphorous compound to a surface-crosslinked water absorbing resin containing a chelating agent.

Taking the manufacturing method as an example, the present invention provides a novel particulate water absorbing agent. The present invention provides a particulate water absorbing agent which is composed primarily of a polyacrylic acid- or polyacrylate-based water absorbing resin and which contains a chelating agent and a phosphorous compound.

Due to the arrangement, the present invention delivers, for example, a good balance of the absorption capacity against pressure (AAP), the centrifuge retention capacity (CRC), the liquid permeability under load (0.69 mass % saline flow conductivity, SFC), good physical properties, good urine resistance (gel degradation prevention property), and a good anti-coloring effect, all ideal for sanitary articles.

If oxycarboxylic acid (hydroxy carboxylic acid) is added to the water absorbing resin as in the technique disclosed in, for example, Japanese Unexamined Patent Publications (Tokukai) Nos. 2000-327926, 2003-52742, and 2005-186016, the necessary water absorbing properties, especially the liquid permeability under load (SFC), deteriorate because the there exists the oxycarboxylic acid (hydroxy carboxylic acid) near the surface of the particulate water absorbing agent, and the existence affects the reactivity of the surface crosslinking agent or the polyvalent metal salt. The techniques disclosed in Japanese Unexamined Patent Publications (Tokukai) Nos. 2003-206305 and 2003-206381 and International Patent Application Published under the PCT, No. WO2005/012369 deliver almost no anti-coloring effect and only poor water absorbing properties.

Conventional art has shown that transition metal ions change color over time during the storage of the water absorbing agent and suggests techniques to let a chelating agent capture a transition metal salt inside the water absorbing resin so as to prevent gel degradation and coloring over time. If a chelating agent alone is added during polymerization, the chelating agent needs to be used in a large amount to deliver effects (gel degradation prevention and temporal coloring prevention effect) desired with a very high quality water absorbing agent. The addition in large amounts can lead to slow or runaway polymerization reaction.

If a chelating agent is added alone to the obtained water absorbing resin, the water absorbing capability (liquid permeability and other absorbing properties, and surface tension) of the water absorbing agent deteriorate.

If the hypophosphorous acid that is a reducing phosphorous compound disclosed in International Patent Application Published under the PCT, No. WO2000/55245 is added to the water absorbing resin, a large amount needs to be added to deliver desired anti-coloring effect. The addition in large amounts can lead to degradation of water absorbing properties, especially the absorption capacity against pressure and the liquid permeability under load.

In the present invention, the combined use of a chelating agent and a phosphorous compound remarkably improves gel degradation prevention and temporal coloring prevention effect to the extent that one could not even image with conventional art. The present invention also reduces the amounts of the chelating agent and the phosphorous compound used. Furthermore, the present invention advantageously achieves improvements in water absorbing properties (especially, liquid permeability under load), anti-gel degradation effect, and anti-coloring effect, which normally would be incompatible.

Conventionally, gel degradation prevention and temporal anti-coloring have been assumed to be caused by oxidation of an inhibitor in the main chain of a water absorbing resin and a monomer and triggered by transition metal ions. We have found in the present invention it is indeed transition metal ions, especially iron ions, that act as the trigger. Meanwhile, transition metal ions, especially iron ions, are effective in controlling polymerization reaction and surface crosslinking reaction and if adjusted to a predetermined amount, also effective in improving absorbing properties.

Neither the use of a chelating agent alone nor the use of a reducing substance alone delivers sufficient urine resistance (gel degradation prevention), coloring prevention, or temporal coloring prevention effect. To deliver sufficient effect, it has been regarded that it is necessary to add an amount that would sacrifice the water absorbing capability which has been pursued in the first place.

A phosphorous compound and a chelating agent are used together in the present invention regardless of the presence/absence of reducing property. Thus, although detailed reaction mechanism is yet to be known, the invention is safely assumed to be realizing excellent urine resistance (gel degradation prevention), coloring prevention, temporal coloring prevention effect, and absorbing capability because it is dramatically effective in the stabilization of transition metal ions, especially iron ions.

Furthermore, an example of most preferred embodiments of the particulate water absorbing agent of the present invention is a particulate water absorbing agent having a chelating agent therein and a phosphorous compound on or near the surface. Especially, the phosphorous compound preferably distributes near the surface layer of the water absorbing agent where the agent contacts oxygen. In addition, the chelating agent distributes inside the water absorbing agent particles and therefore successfully delivers improvements in water absorbing properties (especially, liquid permeability under load), anti-gel degradation effect, and anti-coloring effect, which normally would be highly incompatible.

The distribution of the phosphorous compound and the chelating agent in the water absorbing agent can be determined. For example, the surface of particles may be polished with a high speed homogenizer. The polished water absorbing agent or its surface layer is then extracted for elemental analysis and detection. Quantitative analysis may be performed after extraction in a hydrophilic organic solvent. Alternatively, the distribution of phosphor in the particles may be measured by dying with a compound which colors when reacting with a phosphorous compound. The water absorbing agent can be polished by, for example, the method described in U.S. Pat. No. 6,562,879. The polished water absorbing agent can be separated from the detached surface layer by, for example, classification using a sieve with 150-μm openings.

The iron content (expressed in terms of $Fe_2O_3$) relative to the particulate water absorbing agent is controlled to preferably 0 to 3 mass ppm, more preferably 0.0001 to 2 mass ppm, most preferably 0.001 to 1 mass ppm, in the present invention to achieve high absorbing capability.

The iron content is controlled, for example, by controlling the iron content in the neutralize agent, such as sodium hydroxide and potassium hydroxide, which is used to neutralize acrylic acid, by controlling the iron content in, for example, aluminum sulfate used in the surface treatment of the polyvalent metal, or by adding a predetermined amount by a predetermined amount of iron chloride or another water-soluble iron salt compound.

The particulate water absorbing agent of the present invention provides a novel particulate water absorbing agent, that is, provides a novel particulate water absorbing agent that meets at least one of (a) to (c) below.

(a) 150-μm or smaller particles account for 0 to 5 mass %. The mass-average particle diameter (D50) is 200 to 600 μm. The logarithmic standard deviation (σζ) of the particle size distribution is 0.20 to 0.50.

(b) The absorption capacity against pressure (AAP) for a 0.90-mass % aqueous solution of sodium chloride under 1.9 kPa or 4.9 kPa in 60 minutes is at least 20 g/g.

(c) The 0.69-mass % saline flow conductivity (SFC) is at least 5 $(cm^3 \cdot sec \cdot 10^{-7} \cdot g^{-1})$.

The novel particulate water absorbing agents which meet at least one of (a) to (c) above invariably contain a chelating agent and a phosphorous compound, preferably meet one of the combinations of (a) and (b), (a) and (c), and (b) and (c), and more preferably meet all of (a) to (c). The following will describe properties (a) to (c), and more preferably met properties (d) to (g), of the particulate water absorbing agent of the present invention.

(a) Particle Size

The particulate water absorbing agent of the present invention is controlled to the following, preferably specific, particle size. The particle size is adjusted appropriately by pulverization, classification, agglomeration, collection of fine particles, etc.

The mass-average particle diameter (D50) of the particulate water absorbing agent is 200 to 600 μm, preferably 250 to 550 μm, more preferably 200 to 500 μm, even more preferably 350 to 450 μm. There should be as few 150-μm or smaller particles as possible. After the adjustment, particles of that size account for usually 0 to 5 mass %, preferably 0 to 3 mass %, more preferably 0 to 1 mass %. There should be as few 850-μm or greater particles as possible. After the adjustment, particles of that size account for usually 0 to 5 mass %, preferably 0 to 3 mass %, more preferably 0 to 1 mass %. The logarithmic standard deviation (σζ) of the particle size distribution is preferably 0.20 to 0.50, more preferably 0.25 to 0.45, even more preferably 0.25 to 0.40, most preferably 0.25 to 0.35.

Sizes of the particles outside these particle size distributions will degrade the effects of the particles when the particles are used in disposable diapers and other absorbing articles.

The bulk specific gravity (defined in JIS K-3362) is adjusted to preferably 0.40 to 0.90 g/mL, more preferably 0.50 to 0.80 g/mL. Particles measuring 600 to 150 μm account for preferably 60 to 100 mass %, more preferably 70 to 100 mass %, even more preferably 80 to 100 mass %, of the total mass.

(b) Absorption Capacity Against Pressure (AAP, Absorbency Against Pressure)

In the particulate water absorbing agent of the present invention, taking the surface crosslinking as an exemplary means of achieving, the absorption capacity (AAP) for 0.9 mass % sodium chloride under a load (1.9 kPa or 4.9 kPa) is controlled to preferably 20 (g/g) or greater, more preferably 25 (g/g) or greater.

If the absorbing capability (AAP) under 9 kPa or 4.9 kPa is 20 (g/g) or less and if the agent is used in a diaper, for example, there occurs large rewetting, possibly undesirably causing a rash on babies' skin.

(c) Liquid Permeability under Load (0.69 mass % Saline Flow Conductivity, SFC, Saline Flow Conductivity)

In the particulate water absorbing agent of the present invention, taking the surface crosslinking as an exemplary means of achieving, the liquid permeability under load (0.69 mass % saline flow conductivity, SFC) is controlled to preferably 5 ($cm^3 \cdot sec \cdot 10^{-7} \cdot g^{-1}$) or greater, more preferably 10 ($cm^3 \cdot sec \cdot 10^{-7} \cdot g^{-1}$) or greater, even more preferably 30 ($cm^3 \cdot sec \cdot 10^{-7} \cdot g^{-1}$) or greater, still more preferably 50 ($cm^3 \cdot sec \cdot 10^{-7} \cdot g^{-1}$) or greater, yet more preferably 70 ($cm^3 \cdot sec \cdot 10^{-7} \cdot g^{-1}$) or greater, most preferably 100 ($cm^3 \cdot sec \cdot 10^{-7} \cdot g^{-1}$) or greater.

If the SFC is less than 5 ($cm^3 \cdot sec \cdot 10^{-7} \cdot g^{-1}$) and if the concentration of the particulate water absorbing agent in the diaper core is 30 mass % or greater, more specifically 50 mass % or greater, the absorption rate for urine falls, possibly causing leakage.

(d) Centrifuge Retention Capacity (Centrifugal Separator Retention Capacity, CRC)

In the particulate water absorbing agent of the present invention, taking the polymerization as an exemplary means of achieving, the centrifuge retention capacity (CRC) for a 0.9 mass % aqueous solution of sodium chloride is controlled to preferably 10 g/g or greater, more preferably 20 g/g or greater, even more preferably 25 g/g or greater, still more preferably 30 g/g. The greater the CRC, the better. No particular maximum value is specified. The CRC is preferably 50 (g/g) or less, more preferably 45 (g/g) or less, even more preferably 40 (g/g) or less, in view of balance with other physical properties.

If the centrifuge retention capacity (CRC) is 10 (g/g) or less, the agent can absorb too a small quantity to be used in diapers and other sanitary articles. If the centrifuge retention capacity (CRC) is greater than 50 (g/g), the gel strength is so weak that the resultant water absorbing agent may not possess excellent liquid permeability.

(e) Extractable Polymer Content (Soluble Content)

In the particulate water absorbing agent of the present invention, taking the polymerization as an exemplary means of achieving, the amount of extractable polymer content is preferably 0 to 35 mass % or less, more preferably 25 mass % or less, even more preferably 15 mass % or less, still more preferably 10 wt %. If the amount of extractable polymer content exceeds 35 mass %, the gel strength is so weak that the resultant water absorbing agent may possess poor liquid permeability and when used in a diaper for an extended period of time, the absorption capacity (CRC, AAP, etc.) may decrease over time.

(f) Coloring Temporal Stability

The particulate water absorbing agent obtained in the present invention is suitable for use in disposable diapers and other sanitary articles. In such usage, the agent retains an extremely clean, white appearance at high humidity and high temperature throughout a long-term storage. Furthermore, the agent is a water absorbing resin obtained by the manufacturing method detailed earlier. Particles exposed to an atmosphere at 70±1° C. and a relative humidity of 65±1% for 7 days shows an L value (Lightness) of at least 70, preferably 74 or greater, more preferably 78 or greater. The L value is measured by a spectroscopic colorimeter according to Hunter's Lab color system. The agent is color stable over time. The L value usually has a maximum of 100. If the maximum is 70, there is practically no problems in actual use.

b value is 0 to 15, preferably 0 to 12, more preferably 0 to 10. a value is 0 to 3, preferably 0 to 2, more preferably 0 to 1.

Yellowness (YI value/Yellow Index/see European Patents Nos. 942014 and 1108745) is preferably 0 to 15, more preferably 0 to 13, even more preferably 0 to 10, most preferably 0 to 5. The agent shows almost no yellowing. The rate of change of yellowness after an accelerated coloring test at 70° C.±1 and a relative humidity of 65±1% for 7 days (YI value after the test/YI value before the test*100) is 100 to 150%, preferably 100 to 140%, more preferably 100 to 130%, even most preferably 100 to 120%. The test demonstrates that the agent has a surprisingly high anti-yellowing property even at extremely high temperature and humidity.

(g) Residual Monomer

In the particulate water absorbing agent of the present invention, taking the polymerization as an exemplary means of achieving, the amount of the residual monomer is preferably 0 to 400 mass ppm, more preferably 0 to 300 mass ppm, even more preferably 0 to 200 mass ppm, still more preferably 0 to 100 ppm.

(19) Other Additives

Apart from the phosphorous compound and the chelating agent, other additives may be added to the water absorbing resin to give the resin various functions according to its target functionality. Examples include organic acids; oxidants; reducing agents, such as sulfurous acid (hydrogen) salts; water-insoluble inorganic or organic powder, such as silica and metal soap; deodorants; antibacterial agents; polymer polyamine; pulp; and thermoplastic fiber. These additives account for 0 to 3 mass %, preferably 0 to 1 mass %, of the water absorbing resin.

Among these additional additives, a hydroxy acids (salts), such as lactic acid (salt), citric acid (salt), and malic acid (salt), which are listed as examples in Japanese Patent Application (Tokugan) No. 2007-71075, are especially preferably added to the particulate water absorbing agent in the present invention to further improve temporal coloring prevention effect. These a hydroxy acids (salts) may account for 0.1 to 3 mass %, preferably 0.2 to 3 mass %, of the particulate water absorbing agent.

(20) Use

The use of the particulate water absorbing agent of the present invention is not limited in any particular manner. The agent is used preferably in disposable diapers, sanitary napkins, incontinence pads, and other absorbing articles. The agent exhibits especially excellent capability if used in a high concentration diaper (a diaper stuffed with a large quantity of water absorbing resin) which conventionally had odor and coloring problems which came from the raw materials for the particulate water absorbing agent, especially in a higher layer section of the absorbent core of the absorbing articles listed above.

The absorbing article of the present invention is structured from a particulate water absorbing agent, an absorbent core obtained by, if necessary, molding hydrophilic fiber into a sheet, a liquid-passing surface sheet, and a non-liquid-passing back sheet. If the absorbent core contains no hydrophilic fiber, the absorbent core is fabricated by fixing the particulate water absorbing agent to paper and/or nonwoven fabric. If a fiber material (pulp) is used, the material is sandwiched or blended before being molded. Fiber base materials which may be used are crushed wood pulp, cotton linter, crosslinked cellulose fiber, rayon, cotton, wool, acetate, vinylon, and other like hydrophilic fibers. Preferably, these materials are aerated.

The particulate water absorbing agent content of the absorbent core in the absorbing article (core concentration) is 30 to 100 mass %, preferably 40 to 100 mass %, more preferably 50 to 100 mass %, even more preferably 60 to 100 mass %, still more preferably 70 to 100 mass %, most preferably 75 to 95 mass %, to demonstrate the effects of the present invention. For example, if the particulate water absorbing agent of the present invention is used at the concentration, especially, in a higher layer section of the absorbent core, the agent exhibits excellent diffusibility for absorbed liquids, such as urine, due to its high liquid permeability (liquid permeability under load). This efficient liquid distribution in a disposable diaper or like absorbing article improves the amount absorbed by the entire absorbing article and gives the absorbing article with an absorbent core which retains a sanitary feel and remains white.

The absorbent core is preferably compress molded to a density of 0.06 g/cc to 0.50 g/cc inclusive and a basis weight of 0.01 g/cm$^2$ to 0.20 g/cm$^2$ inclusive. The absorbent core has a thickness to 30 mm or less, preferably 20 mm or less and thereby provides an absorbing article suitable for use in thin disposable diapers.

EXAMPLES

The following will describe the invention by way of examples. The examples are given for illustrative purposes only and by no means limit the scope of the present invention. Physical properties (a) to (g) described in claims and examples of the invention were measured by the following methods. The following measuring methods are described in connection with particulate water absorbing agents. The methods however are applicable to water absorbing resins simply by replacing "particulate water absorbing agent" with "water absorbing resin" in the description. "Mass" and "weight" are synonymous. For example, "mass ppm" and "weight ppm" are synonyms throughout the specification.

(a) Particle Size

The water absorbing resin (or particulate water absorbing agent) was sieved, according to WO2004/069404, using JIS (JIS Z8801-1 (2000))-compliant or equivalent sieves having mesh opening sizes of 850 μm, 710 μm, 600 μm, 500 μm, 425 μm, 300 μm, 212 μm, 150 μm, 106 μm, and 45 μm. The residual percentages R were plotted on a logarithm probability sheet. From the plots, the particle diameter which corresponds to R=50 wt % was read off as the weight-average particle diameter (D50). The logarithmic standard deviation, σζ, is given by the following equation 1. The smaller the value of σζ, the narrower the particle size distribution.

$$\sigma\zeta = 0.5 \times \ln(X2/X1) \qquad \text{Eq. 1}$$

where X1 and X2 are particle diameters for R=84.1% and R=15.9% respectively.

(b) Absorption Capacity Against Pressure (AAP)

The absorption capacity under pressure (under load) was measured for a 0.9% aqueous solution of sodium chloride according to International Patent Applications Published under the PCT, Nos. WO2006/109844 and WO2007/JP/56527.

A stainless-steel 400 mesh (mesh size of 38 μm) was welded onto a side (bottom) of a cross-section of a plastic supporting cylinder having an internal diameter of 60 mm. Then, 0.900 g of the water absorbing resin (or particulate water absorbing agent) was evenly sprayed onto that metal net on the bottom. A piston (cover plate) was placed on the sprayed resin. The piston had an external diameter slightly less than 60 mm. The piston left no space between itself and the wall surface of the supporting cylinder, but its vertical motions were not disrupted. The combined mass W3 of the supporting cylinder, the water absorbing resin (or particulate water absorbing agent), and the piston was measured in grams. Subsequently, a load was placed on the piston. The load had been adjusted so that the combination of the load and the piston could evenly apply a pressure of 1.9 kPa or 4.9 kPa to the water absorbing resin (or particulate water absorbing agent). Assembly of a set of measuring device was thus completed. A 5-mm thick glass filter with a diameter of 90 mm was placed in a petri dish with a diameter of 150 mm. A physiological saline (temperature adjusted to 25±2° C.) was added until it was flush with the top face of the glass filter. A sheet of filter paper (No. 2 manufactured by Toyo Roshi Kaisha, Ltd.) with a diameter of 9 cm was placed on top of that so that the entire surface was wet, and excess solution.

The set of measuring device was placed on the wet filter paper so that the paper could absorb the solution under the load. The solution was added if its surface lowered from the top face of the glass filter, so as to maintain a constant liquid surface level. An hour later, the set of measuring device was lifted, and the combined mass W4 (g) of the supporting cylinder, the swollen water absorbing resin (or particulate water absorbing agent), and the piston (excluding the load) was measured. The values were substituted into W3, W4 in the equation below to calculate an absorption capacity against pressure (g/g).

$$\text{Absorption Capacity against Pressure}(AAP;0.90g)(g/g) = (\text{Mass } W4(g) - \text{Mass } W3(g))/\text{Mass}(g) \text{ of Water Absorbing Resin(or Particulate Water Absorbing Agent)}$$

(c) 0.69 Mass % Saline Flow Conductivity (SFC)

69 mass % saline flow conductivity (SFC) is a value indicating the liquid permeability of water absorbing resin particles or a particulate water absorbing agent when the particles/agent is/are swollen. The greater the value of SFC, the greater liquid permeability the resin/agent possesses. The tests were carried out in the same manner as the SFC test described in the specification of U.S. Pat. No. 5,849,405.

The water absorbing resin particles or particulate water absorbing agent (0.900 g) was/were placed evenly in a container (40) and let to swell in artificial urine (1) under a load of 0.3 psi (2.07 kPa) for 60 minutes. The height of the layer of the gel (44) was recorded. Next, the 0.69 mass % aqueous solution of sodium chloride (33) was fed from the tank (31) to pass through the swollen gel layer under a load of 0.3 psi (2.07 kpa) at a constant hydrostatic pressure. The SFC test was conducted at room temperature (20 to 25° C.). The amount of the solution that had passed through the gel layer was recorded using a computer and scales (49) as a function of time at 20-second intervals for 10 minutes. The flow rate Fs(T) at which the solution passed through the swollen gel (44) (primarily between particles) was determined in units of grams per second (g/s) by dividing an increase in mass (g) by an increase in time (s). Flow rates were calculated from the data obtained in the 10 minute period starting at time Ts at which a constant hydrostatic pressure and a stable flow rate were achieved. The value of Fs(T=0), or the flow rate at which the solution first passed through the gel layer, was calculated from the flow rates obtained in the 10 minute period starting at Ts. The value of Fs(T=0) was obtained by extrapolating, for T=0, the result of least square approximation of Fs(T) vs. time.

$$0.69 \text{ Mass \% Saline Flow Conductivity}(SFC) = (Fs(T=0) \times L0)/(\rho \times A \times \Delta P) = (Fs(T=0) \times L0)/139506 \qquad \text{Eq. 2}$$

where Fs(T=0) is the flow rate in grams per second; L0 is the height of the gel layer in centimeters; ρ is the density of the NaCl solution (1.003 g/cm$^3$); A is the area of the top face of the gel layer in the cell 41 (=28.27 cm$^2$); and ΔP is the hydrostatic pressure exerted on the gel layer (=4,920 dyne/cm$^2$). The values of SFC were given in units of cm$^3$·sec·10$^{-7}$·g$^{-1}$.

Artificial urine (1) was a mixture of 0.25-gram calcium chloride dihydrate, 2.0-gram potassium chloride, 0.50-gram magnesium chloride hexahydrate, 2.0-g sodium sulfate, 0.85-gram ammonium dihydrogenphosphate, 0.15-gram diammonium hydrogenphosphate, and 994.25-gram pure water.

(d) Centrifuge Retention Capacity (GVs/CRC)

0.2-gram of the particulate water absorbing agent was placed evenly in a bag of nonwoven fabric (60×60 mm) and sealed. The bag was immersed in 100 grams of a 0.9 mass % aqueous solution of sodium chloride (also called physiological saline) at 25° C. (±3° C.). After 60 minutes, the bag was taken out of the solution and centrifuged for 3 minutes in a centrifugal separator at 250 G to remove water from the bag. The mass W1 of the nonwoven fabric bag was measured. The same process was carried out using no particulate water absorbing agent, and the mass W2 was measured. An absorption capacity was calculated using equation 3.

$$GVs=(W1-W2)/0.2-1 \quad \text{Eq. 3}$$

(e) Extractable Polymer Content (also termed "Extractable Content" or "Water-soluble Content")

184.3 g of the 0.90 wt % aqueous solution of sodium chloride was prepared in a lidded plastic container (capacity: 250 mL). 1.00 g of the particulate water absorbing agent was added to the aqueous solution and stirred for 16 hours to extract extractable content of the resin. The liquid extract was filtered through a paper filter ("JIS P 3801, No. 2," Advantec Toyo Kaisha, Ltd.; thickness 0.26 mm, retainable particle diameter 5 µm). 50.0 g of the obtained filtrate was set aside for measurement as a sample solution.

The physiological saline alone was titrated first to pH 10 with a 0.1 N aqueous solution of NaOH and thereafter to pH 2.7 with a 0.1 N aqueous solution of HCl, to determine a blank titer ([bNaOH] mL, [bHCl] mL). The same titration was performed on the sample solution to determine a titer ([NaOH] mL, [HCl] mL). If the particulate water absorbing agent is composed of known amounts of an acrylic acid and its salt, for example, the soluble content of the particulate water absorbing agent (composed primarily of extracted extractable polymer content) can be calculated from the average molecular weight of the monomer and the titer determined by the operation using equation 8 below. If the particulate water absorbing agent is composed of unknown amounts of an acrylic acid and its salt, the average molecular weight of the monomer is calculated from the neutralization ratio determined by the titration.

$$\text{Soluble Content(wt \%)}=0.1\times(\text{Average Molecular Weight})\times184.3\times100\times([\text{HCl}]-[\text{bHCl}])/1{,}000/1.0/50.0 \quad \text{Eq. 4}$$

$$\text{Neutralization Ratio(mol \%)}=(1-([\text{NaOH}]-[\text{bNaOH}])/([\text{HCl}]-[\text{bHCl}]))\times100 \quad \text{Eq. 5}$$

(f) Assessment of Coloring of Particulate Water Absorbing Agent

The coloring of the particulate water absorbing agent was assessed by a spectroscopic calorimeter, "SZ-Σ80 color measuring system," manufactured by Nippon Denshoku Industries Co., Ltd. Specifically, the measurement was conducted by reflection measurement. A powder/paste container which had come with the system was used. The container had an internal diameter of 30 mm and a height of 12 mm. A powder/paste standard round white board No. 2 was used as a standard. A 30Φ light projection pipe was used. The powder/paste container which had come with the system was charged with about 5 g of the water absorbing polymer. By that charging, the powder/paste container was filled up to about 60%. The surface L value (Lightness: luminosity index) was measured with the spectroscopic calorimeter at room temperature (20 to 25° C.) and 50 RH % of humidity. This value was designated a pre-spray luminosity index.

Object colors a, b (chromaticity), YI (yellowness), and WB (white balance) can also be measured on different scales simultaneously by the same measuring method using the same device. The greater the value of WB, the less the coloring (the whiter). The smaller the values of YI, a, and b, the less the coloring (the whiter).

Subsequently, the powder/paste container was charged with about 5 g of the particulate water absorbing agent. The powder/paste container charged with the water absorbing polymer was exposed to an atmosphere at 70±1° C. and relative humidity 65±1% for 7 days in a thermo-hygrostat (compact environment tester series "SH-641" manufactured by Tabai Espec Corporation). This exposure was a 7-day long accelerated coloring test. After the exposure, the surface L value (Lightness) of measure with the spectroscopic calorimeter. The measurement was designated the L value of particles exposed to an atmosphere at 70±1° C. and relative humidity 65±1% for 7 days in a Hunter Lab color system.

(g) Residual Monomer

Regarding the residual monomer (residual acrylic acid (acrylate)) in the particulate water absorbing agent, a filtrate which was extracted by the same procedures as in (e) above. 184.3 g of the 0.90 wt % aqueous solution of sodium chloride was prepared in a lidded plastic container (capacity: 250 mL). 1.00 g of the particulate water absorbing agent was added to the aqueous solution and stirred for 2 hours to extract extractable content of the resin. After 2 hours, the liquid extract was filtered through a paper filter used in (e) to collect filtrate. By analyzing, under UV by liquid chromatography, the filtrate, the amount of the residual monomer (ppm) (relative to the particulate water absorbing agent) of the particulate water absorbing agent was analyzed. In addition, the amount of the residual monomer of the pre-drying water-containing gel was determined by stirring a crushed water-containing gel containing about 500 mg resin solid content for 16 hours, analyzing its filtrate thereof similarly under UV by liquid chromatography, and correcting data with respect to solid content.

The solid content (%) was measured as below.

First, 1 gram of a water absorbing agent placed in an aluminum cup (bottom diameter: 52 mm, height: 22 mm) was dried for 3 hours in a homothermal drier at 180° C. (NDO-450 available from Tokyo Rikakikai Co., Ltd.). The solid content (%) was obtained from the masses before and after the drying. In the case of measuring the solid content in a water-containing gel, the gel was dried for 12 hours in a homothermal drier at 180° C.

$$\text{Solid Content(\%)}=100-[\text{Pre-drying Mass}(g)-\text{Post-drying Mass}(g)/\text{Pre-drying Mass}(g)]\times100$$

(h) GEX Value

A GEX value was calculated according to the description of U.S. Patent No. 20060167198. Letting y (g/g) be the value of centrifuge retention capacity and x (mass %) be the amount of extractable polymer content, the GEX value is defined by the equation below:

$$GEX \text{ Value}=(y+17)/\ln(x), x>1 \quad \text{Eq. 6}$$

where ln (x) is the natural logarithm of x

The GEX value enables a single parameter to represent an evaluation of the relationship between GV values and soluble content (a low amount of soluble content relative to a GV value is good and a large amount of soluble content relative to a GV value is poor). The greater the GEX value, the higher the capability. If x≤1, the GEX value is defined by the equation below:

$$GEX \text{ Value}=(y)/(x) \qquad \text{Eq. 7}$$

Manufacturing Example 1

0.10 mol % polyethylene glycol diacrylate (relative to the whole monomer) was dissolved in 5,500 grams of an aqueous solution of sodium acrylate (monomer concentration 37.2 wt %) having a neutralization ratio of 75 mol % in a reaction vessel which was a lidded stainless steel double-arm kneader with two sigma-type blades and a jacket (internal volume 10 L) to obtain a reaction solution. This polyethylene glycol diacrylate as an internal crosslinking agent had an average number of ethylene oxide added of 9 moles. Furthermore, the sigma-type double-arm kneader was charged with the reaction solution while being maintained at 25° C. A nitrogen gas was blown into the kneader to substitute nitrogen for oxygen so as to reduce the oxygen remaining dissolved in the system to 1 mass ppm or less. Subsequently, 27.7 g of a 10 wt % aqueous solution of sodium persulfate and 2.31 g of a 1 wt % aqueous solution of L-ascorbic acid were added to the reaction solution while stirring. About 30 seconds after the addition, the reaction solution heated to 25.5° C. when polymerization started.

The polymerization proceeded while crushing the gel generated by the polymerization. 14 minutes into the polymerization, the reaction solution showed a polymerization peak temperature of 90° C. After reaching the polymerization peak, the jacket temperature was kept at 60° C. for another 20 minutes. A water-containing gel-like crosslinked polymer was taken out 34 minutes into the polymerization. The obtained water-containing gel-like crosslinked polymer had been crushed to a diameter of about 5 mm or less. The crushed water-containing gel-like crosslinked polymer was spread on a 20 mesh (mesh size of 850 μm) metal net and dried in a heated air flow at 180° C. for 45 minutes. Next, the polymer was pulverized in a roll mill and subjected to a classification using JIS standard sieves having mesh sizes of 850 μm and 150 μm. The result was dry powder (a) having a weight-average particle diameter of 350 μm and σζ of 0.35 and containing 2% particles that were 150 μm or smaller.

Table 1 shows physical properties of obtained dry powder (a).

Manufacturing Example 2

The device shown in FIG. 3 of U.S. Patent Application Publication No. 2004/0092688A1 was used in the following manufacture. First, the device was set up for the following flow rates: 5.13 g/s for a 48.5 wt % aqueous solution of sodium hydroxide; 6.09 g/s for acrylic acid; 0.15 g/s for a 30 wt % aqueous solution of polyethylene glycol diacrylate (I); 0.16 g/s for a solution (II), which was a mixture of 50.0 parts by mass of a 1.0 wt % acrylic acid solution of 2-hydroxy methyl-2-methyl propiophenone and 50.0 parts by mass of a 0.93 wt % aqueous solution of trisodium diethylenetriamine pentaacetate (abbreviated as DTPA·3Na); and 4.63 g/s for water. A monomer liquid 20 was prepared using the device shown in FIG. 3 of U.S. Patent Application Publication No. 2004/0092688A1.

The temperature of the monomer liquid 20 was stable at about 95° C. This polyethylene glycol diacrylate as an internal crosslinking agent had an average number of ethylene oxide added of 9 moles. The monomer liquid 20 was stirred in a stirrer (static mixer) having an element with a length of 18.6 mm and a diameter of 6 mm twisted by 1.5 turns and inserted in a tube (diameter=6 mm). After the stirring, the monomer liquid 20 was mixed with a 2 wt % aqueous solution of sodium persulfate (polymerization initiator) about 3 cm downstream from the terminating end of the element where the aqueous solution flows into the element at a flow rate of 0.511 g/s, to produce a mix solution 40. The mix solution 40 was fed to a belt polymerization device 70 for continuous polymerization to obtain a belt-like polymer gel. The device 70 had an endless belt which was 3.8 m long and 60 cm wide and of which the surface was coated with fluorine resin. A UV lamp was disposed over the belt. The bottom face of the device 70 and its proximity were heated and maintained at about 100° C. The device 70 also had an air intake tube disposed at the center to collect evaporated water. The length of the path from the site where the flow of the polymerization initiator merged to an outlet of the polymerization device was 30 cm.

The belt-like polymer gel of which the surface temperature was about 70° C. was crushed continuously with a meat chopper, dried in a heated air flow at 180° C. to obtain a dry product pulverized in a roll mill, and subjected to a classification using JIS standard sieves having mesh sizes of 850 μm and 150 μm. The result was dry particles (b) having a weight-average particle diameter of 350 μm and σζ of 0.36 and containing 2% particles that were 150 μm or smaller.

Surface Crosslinking Agent

The surface crosslinking agent had the same composition throughout the examples and comparative examples presented later as in example 1 and heated at 210° C. for 40 minutes, unless otherwise stated.

Polyvalent Metal Salt

The aluminum sulfate (abbreviated as ASH) processing liquid used in example 2 and elsewhere was obtained by adding 0.3 parts by mass of a 60% aqueous solution of sodium lactate (manufactured by Musashino Chemical Laboratory, Ltd.) to 1.0 parts by mass of a 50 mass % solution of liquid aluminum sulfate for tap water use (manufactured by Asada Chemical Industry Co., Ltd.) and further mixing with 0.025 parts by mass propylene glycol. The aluminum sulfate processing liquid was used for the surface treatment of the polyvalent metal unless otherwise stated.

Examples 1 to 5

In examples 1 to 5 below, 100 ppm (to 1,000 ppm) DTPA·3Na was used as the chelating agent in polymerization. Also, phosphoric acid (salt) was added as the equal moles of phosphorous compound simultaneously with or after the surface crosslinking for comparison of coloring over time.

Example 1

A surface crosslinking agent composed of 0.4 parts by mass 1,4-butanediol, 0.6 parts by mass propylene glycol, 3.0 parts by mass ion exchange water, and 0.5 parts by mass isopropanol was sprayed and mixed with 100 parts by mass of dry powder (b) obtained by using a chelating agent, DTPA·3Na (100 ppm), in the polymerization manufacturing example 2. The mixture was then heated at 210° C. for 40 minutes to obtain water absorbing resin (1).

Next, 40 mass % sodium dihydrogenphosphate (abbreviated as SDP) as s phosphorous compound was added (and mixed) up to 6,200 mass ppm (relative to the solid content of the water absorbing resin) to 100 parts by mass of surface crosslinked water absorbing resin (1) containing 100 ppm of the chelating agent therein. The mixture was moved to a plastic bag with a zipper, "Unipack" (trade name of a product manufactured by Seisan Nipponsha Ltd.) and sealed. The bag was heated in a drying device (no air flow) at 60° C. for 30 minutes to obtain particulate water absorbing agent (1).

Example 2

The same procedures were taken as in manufacturing example 2 except that the concentration of the aqueous solution of the chelating agent DTPA·3Na in the polymerization was changed to 9.3 wt % (1,000 ppm). 100 parts by mass of obtained dry powder (b) was subjected to surface crosslinking as in example 1 to obtain water absorbing resin (2).

85 mass % phosphoric acid (equal moles to example 1) was added (and mixed) up to 5,000 mass ppm to 100 parts by mass of water absorbing resin (2) containing 1,000 ppm of the chelating agent therein. The aluminum sulfate (abbreviated as ASH) processing liquid was then added up to 1.26 parts by mass. The mixture was dried in a heated air flow at 60° C. for 1 hour for surface treatment with polyvalent metal salt to obtain particulate water absorbing agent (2).

Example 3

1.26 parts by mass of the aluminum sulfate processing liquid used in example 2 was added to 100 parts by mass of water absorbing agent (1) obtained in example 1 and dried in a heated air flow at 60° C. for 1 hour for surface treatment with polyvalent metal salt to obtain particulate water absorbing agent (3).

Example 4

In example 1, the phosphorous compound was added in 6,200 ppm after surface crosslinking. Instead, the phosphorous compound was added during (simultaneously) the surface crosslinking. In other words, in example 4, surface crosslinking was carried out similarly to example 1, but by adding 0.62 parts by mass (6,200 ppm) SDP to the surface crosslinking agent to obtain particulate water absorbing agent (4).

Example 5

1.26 parts by mass of aluminum sulfate processing liquid of example 2 was added to 100 parts by mass of particulate water absorbing agent (4) obtained in example 4 and dried in a heated air flow at 60° C. for 1 hour for surface treatment with polyvalent metal salt to obtain particulate water absorbing agent (5).

Examples 6 to 10

In examples 6 to 10 below, 100 ppm (to 1,000 ppm) tetrasodium 3-hydroxy-2,2'-iminodisuccinate (abbreviated as HIDS) was used as the chelating agent in polymerization. Also, phosphoric acid (salt) was added as the equal moles of phosphorous compound simultaneously with or after the surface crosslinking for comparison of coloring over time.

Example 6

The same procedures were taken as in manufacturing example 2 except that an aqueous solution of the chelating agent (HIDS) was used in place of the aqueous solution of the chelating agent DTPA·3Na used in the polymerization in manufacturing example 2, to obtain dry powder (c). Next, 100 parts by mass of obtained dry powder (c) was subjected to surface crosslinking as in example 1 to obtain water absorbing resin (5).

Next, similarly to example 1, 40 mass % SDP was added (and mixed) up to 6,200 mass ppm to 100 parts by mass of water absorbing resin (5) containing 100 ppm of the chelating agent (HIDS) therein. Particulate water absorbing agent (6) was hence obtained.

Example 7

The same procedures were taken as in manufacturing example 2 except that a 9.3 mass % (1,000 ppm) aqueous solution of HIDS was used in place of the aqueous solution of DTPA·3Na, to obtain dry powder (d). Dry powder (d) obtained was subjected to surface crosslinking as in example 1 to obtain water absorbing resin (6).

Next, 85 mass % phosphoric acid was added (and mixed) up to 5,000 mass ppm (equal moles) to 100 parts by mass of water absorbing resin (6) containing 1,000 ppm of the chelating agent (HIDS) therein. Particulate water absorbing agent (7) was hence obtained.

Example 8

100 parts by mass of particulate water absorbing agent (6) obtained in example 6 was further processed with aluminum sulfate similarly to example 2. Particulate water absorbing agent (8) was hence obtained.

Example 9

In example 6, the phosphorous compound was added in 6,200 ppm after surface crosslinking. Instead, the phosphorous compound was added during (simultaneously) the surface crosslinking. In other words, in example 9, surface crosslinking was carried out similarly to example 6, but by adding 0.62 parts by mass (6,200 ppm) SDP to the surface crosslinking agent to obtain particulate water absorbing agent (9).

Example 10

100 parts by mass of particulate water absorbing agent (9) obtained in example 9 was further processed with aluminum sulfate similarly to example 2. Particulate water absorbing agent (10) was hence obtained.

Example 11 to 19

In examples 11 to 19 below, 80 ppm (to 200 ppm) EDTMP·5Na was used as the chelating agent in the polymerization. Also, phosphoric acid (salt) was added as the equal moles phosphorous compound simultaneously with or after the surface crosslinking for comparison of coloring over time.

Example 11

0.10 mol % polyethylene glycol diacrylate (relative to the whole monomer) was dissolved in 5,500 grams of an aqueous solution of sodium acrylate (monomer concentration 37.2 wt %) having a neutralization ratio of 75 mol % in a reaction vessel which was a lidded stainless steel double-arm kneader with two sigma-type blades and a jacket (internal volume 10 L) to obtain a reaction solution. This polyethylene glycol diacrylate as an internal crosslinking agent had an average number of ethylene oxide added of 9 moles. Furthermore, the sigma-type double-arm kneader was charged with the reaction solution while being maintained at 25° C. A nitrogen gas was blown into the kneader to substitute nitrogen for oxygen so as to reduce the oxygen remaining dissolved in the system to 1 mass ppm or less. Subsequently, 27.7 g of a 10 wt % aqueous solution of sodium persulfate and 2.31 g of a 1 wt % aqueous solution of L-ascorbic acid were added to the reaction solution in the reaction container while stirring. About 20 seconds after the addition, the reaction solution heated to 25.5° C. when polymerization started. 8.2 g (80 mass ppm relative to the whole monomer) of an 2 mass % aqueous solution of pentasodium ethylenediamine tetra(methylene phosphonate) (abbreviated as EDTMP·5Na) was added to the system 3 minutes into the polymerization.

The polymerization proceeded while crushing the gel generated by the polymerization. 14 minutes into the polymerization, the reaction solution showed a polymerization peak temperature of 96° C. After reaching the polymerization peak, the jacket temperature was kept at 60° C. for another 20 minutes. A water-containing gel-like crosslinked polymer was take out 34 minutes into the polymerization.

The obtained water-containing gel-like crosslinked polymer had been crushed to a diameter of about 5 mm or less. The crushed water-containing gel-like crosslinked polymer was spread on a 20 mesh (mesh size of 850 μm) metal net and dried in a heated air flow at 180° C. for 45 minutes. Next, the polymer was pulverized in a roll mill and subjected to a classification using JIS standard sieves having mesh sizes of 850 μm and 150 μm. The result was dry powder (e) having a weight-average particle diameter of 350 μm and σζ of 0.35 and containing 2% particles that were 150 μm or smaller.

Subsequently, dry powder (e) was subjected to surface crosslinking similarly to examples 1 to 9 to obtain water absorbing resin (7).

85 mass % phosphoric acid was added (and mixed) up to 5,000 mass ppm to 100 parts by mass of water absorbing resin (7). 1.26 parts by mass of the aluminum sulfate processing liquid of example 2 was then added. The mixture was dried in a heated air flow at 60° C. for 1 hour for surface treatment with polyvalent metal salt to obtain particulate water absorbing agent (11).

Example 12

The same procedures were taken as in example 11 except that the amount of the 85% phosphoric acid added after the polymerization was changed to 10,000 mass ppm (in terms of equivalent solid content) to obtain particulate water absorbing agent (12).

Example 13

The same procedures were taken as in example 11 except that the amount of the pentasodium ethylenediamine tetra (methylene phosphonate) added in the polymerization was changed to 200 mass ppm and also that after the polymerization, a 20% aqueous solution of sodium hypophosphite (abbreviated as SHP), in place of the 85% phosphoric acid, was added in the amount of 3,000 mass ppm. Particulate water absorbing agent (13) was hence obtained.

Example 14

The same procedures were taken as in example 11 except that after the polymerization, a 40 mass % sodium dihydrogenphosphate, in place of the 85% phosphoric acid, was added in the amount of 3,100 mass ppm (in terms of equivalent solid content; half moles). Particulate water absorbing agent (14) was hence obtained.

Example 15

The same procedures were taken as in example 11 except that the amount of the chelating agent added in the polymerization was changed. In other words, 20.5 g (200 mass ppm relative to the whole monomer) of a 2 mass % aqueous solution of pentasodium ethylenediamine tetra(methylene phosphonate) was added to the system 3 minutes into the polymerization. Subsequently, the polymer was, similarly example 11, crushed, dried, and pulverized to obtain dry powder (f) having a weight-average particle diameter of 350 μm and σζ of 0.35 and containing 2% particles that were 150 μm or smaller.

Subsequently, a surface crosslinking agent composed of 0.4 parts by mass 1,4-butanediol, 0.6 parts by mass propylene glycol 3.0 parts by mass ion exchange water, 0.5 parts by mass isopropanol, and 0.31 parts by mass SDP was sprayed and mixed with 100 parts by mass of dry powder (f) containing 200 ppm of the chelating agent. The mixture was then heated at 210° C. for 40 minutes to obtain particulate water absorbing agent (15).

Example 16

The amount of the phosphorous compound added to the surface crosslinking agent example 15 was doubled. In other words, the same procedures were taken as in example 15 except that the amount of the 40 mass % aqueous solution of sodium dihydrogenphosphate added to the surface crosslinking agent was changed to 1.55 parts by mass (6,200 mass ppm in the entire powder). Particulate water absorbing agent (16) was hence obtained.

Example 17

The same procedures were taken as in example 13 except that the phosphorous compound added to the surface crosslinking agent was changed from 20 mass % SHP to 40 mass % sodium dihydrogenphosphate and also that the amount added was 0.76 mass % (3,100 mass ppm). Particulate water absorbing agent (17) was hence obtained.

Example 18

100 parts by mass of particulate water absorbing agent (15) obtained in example 15 was subjected to surface treatment with polyvalent metal salt similarly to examples 2 and 11 to 13. Particulate water absorbing agent (18) was hence obtained.

Example 19

100 parts by mass of particulate water absorbing agent (16) obtained in example 16 was subjected to surface treatment with polyvalent metal salt similarly to example 18. Particulate water absorbing agent (19) was hence obtained.

Example 20

A surface crosslinking agent composed of 0.33 parts by mass 1,4-butanediol, 0.54 parts by mass propylene glycol, 2.83 parts by mass ion exchange water, 0.0005 parts by mass polyoxyethylene sorbitan monostearate (trade name: "Rheodol TW-S120," manufactured by Kao Corporation) was sprayed and mixed with 100 parts by mass of dry powder (f) containing 200 mass ppm of the chelating agent obtained in example 15. The mixture was then heated at 210° C. for 40 minutes to obtain a particulate water absorbing agent.

40 mass % sodium dihydrogenphosphate was added (and mixed) up to 1.55 parts by mass to 100 parts by mass of the obtained particulate water absorbing agent. 1.26 parts by mass of the aluminum sulfate processing liquid used in example 2 was further added dried in a heated air flow at 60° C. for 30 minutes for surface treatment with polyvalent metal salt to obtain particulate water absorbing agent (20).

Example 21

A surface crosslinking agent composed of 0.33 parts by mass 1,4-butanediol, 0.54 parts by mass propylene glycol, 2.83 parts by mass ion exchange water, and 0.001 parts by mass polyoxyethylene sorbitan monostearate (trade name: "Rheodol TW-S120," manufactured by Kao Corporation) was sprayed and mixed with 100 parts by mass of dry powder (f) containing 200 mass ppm of the chelating agent obtained in example 15. The mixture was then heated at 210° C. for 40 minutes to obtain a particulate water absorbing agent.

0.875 parts by mass of 40 mass % sodium dihydrogenphosphate was added (and mixed) to 100 parts by mass of the obtained particulate water absorbing agent. 0.9 parts by mass of the aluminum sulfate processing liquid used in example 2 was then added to the mixture and dried in a heated air flow at 60° C. for 30 minutes for surface treatment with polyvalent metal salt. Particulate water absorbing agent (21) was hence obtained.

Example 22

A surface crosslinking agent composed of 0.33 parts by mass 1,4-butanediol, 0.54 parts by mass propylene glycol, 2.83 parts by mass ion exchange water, and 0.003 parts by mass polyoxyethylene sorbitan monostearate (trade name: "Rheodol TW-S120," manufactured by Kao Corporation) was sprayed and mixed with 100 parts by mass of dry powder (f) containing 200 mass ppm of the chelating agent obtained in example 15. The mixture was then heated at 210° C. for 40 minutes to obtain a particulate water absorbing agent.

1.55 parts by mass of 40 mass % sodium dihydrogenphosphate was added (and mixed) to 100 parts by mass of the obtained particulate water absorbing agent. 1.26 parts by mass of the aluminum sulfate processing liquid used in example 2 was then added to the mixture and dried in a heated air flow at 60° C. for 30 minutes for surface treatment with polyvalent metal salt. Particulate water absorbing agent (22) was hence obtained.

Example 23

Absorbent cores were fabricated to evaluate capability as absorbent core. Rewet and the appearance of the absorbent cores were evaluated. First, the following will describe how absorbent cores were fabricated for evaluation.

4 parts by mass of particulate water absorbing agent (20) and 1 part by mass of crushed wood pulp were mixed in a mixer without adding water. Next, The obtained mixture was spread on a wire screen (400 mesh (mesh size of 38 μm)) to form a web with a diameter ($\phi$) of 90 mm. The web was then pressed under a pressure of 196.14 kPa (2 kgf/cm$^2$) for 1 minute to obtain absorbent core (1) for evaluation having a basis weight of about 0.05 g/cm$^2$. The method of 10-minute rewetting evaluation will be described next.

The absorbent core for evaluation was placed on a petri dish made by SUS with an internal diameter ($\phi$) of 90 mm. On top of that, nonwoven fabric with a diameter ($\phi$) of 90 mm was spread. Next, 30 mL of physiological saline (0.9 mass % aqueous solution of sodium chloride) was poured over the nonwoven fabric so that the saline could be absorbed under no load for 10 minutes. Thereafter, 30 sheets of filter paper (No. 2 manufactured by Toyo Roshi Kaisha, Ltd.) with an external diameter ($\phi$) of 90 mm (the total weight (W7 (g)) of the paper was measured in advance) were placed on the nonwoven fabric. A piston and weight (a combined weight of 20 kg) with an external diameter ($\phi$) of 90 mm (which applies an even load to the absorbent core, the nonwoven fabric, and the filter paper) were placed on the filter paper. The load was applied for 5 minutes to make the filter paper to absorb the liquid that came out from the absorbent core. Thereafter, the 30 sheets of filter paper was weighed (=W8 (g)), and the value was substituted in the following equation for 10-minute rewetting. The obtained rewetting was 3.8 g.

$$\text{10-minute Rewetting}(g) = W8(g) - W7(g) \qquad \text{Eq.}$$

Absorbent core (1) for evaluation was left inside a thermohygrostat (compact environment tester series "SH-641" manufactured by Tabai Espec Corporation) for 7 days. The thermo-hygrostat was set up to provide an atmosphere of 70±1° C. and relative humidity 65±1%. The appearance of the absorbent core was visually evaluated. The absorbent core looked white and clean.

Comparative Example 1

The same procedures were taken as in manufacturing example 2 except that a 18.7 mass % aqueous solution of sodium hypophosphite (abbreviated as SHP), in place of the aqueous solution of DTPA·3Na, was used. Comparative particulate water absorbing agent (1) was hence obtained.

Comparative Example 2

The same procedures were taken as in example 11 except that the concentration of the aqueous solution of EDTMP·5Na was changed to 20 mass % and the amount of it added was changed to 102.5 g. The polymerization reaction did not complete. No water-containing crosslinked polymer was obtained. No water absorbing agent was therefore obtained.

Comparative Example 3

The same procedures were taken as in example 13 except that no 20 mass % SHP was added. Comparative particulate water absorbing agent (2) was hence obtained.

Comparative Example 4

The same procedures were taken as in example 14 except that 5.9 mass % (5% relative to the whole monomer) of 85% phosphoric acid, in place of the pentasodium ethylenediamine tetra(methylene phosphonate), was added and no 40 mass % sodium dihydrogenphosphate was added. Comparative particulate water absorbing agent (3) was hence obtained.

Comparative Example 5

The surface crosslinking agent of example 1 was sprayed and mixed with 100 parts by mass of dry powder (a) obtained in manufacturing example 1. The mixture was heated at 210° C. for 40 minutes. Comparative particulate water absorbing agent (4) was hence obtained.

Comparative Example 6

1.26 parts by mass of the aluminum sulfate processing liquid of example 2 was added to comparative particulate water absorbing agent (4) of comparative example 5. The mixture was dried in a heated air flow at 60° C. for 1 hour for surface treatment with polyvalent metal salt. Comparative particulate water absorbing agent (5) was hence obtained.

Comparative Example 7

The surface crosslinking agent of example 1 was sprayed and mixed with 100 parts by mass dry powder (a) obtained in manufacturing example 1. The mixture was heated at 210° C. for 40 minutes. Water absorbing resin (8) was hence obtained.

Then, comparative particulate water absorbing agent (6) was obtained.

1.26 parts by mass of the aluminum sulfate processing liquid of example 2 was added to 100 parts by mass of water absorbing resin (8). The mixture was dried in a heated air flow at 60° C. for 1 hour for surface treatment with polyvalent metal salt. Comparative particulate water absorbing agent (6) was hence obtained.

Comparative Example 8

1.26 parts by mass of the aluminum sulfate processing liquid of example 2 was added to comparative particulate water absorbing agent (3) of comparative example 4. The mixture was dried in a heated air flow at 60° C. for 1 hour for surface treatment with polyvalent metal salt. Comparative particulate water absorbing agent (7) was hence obtained.

Comparative Example 9

A 20 mass % aqueous solution of sodium hypophosphite was added to comparative particulate water absorbing agent (4) of comparative example 5 so that the amount added was 1 mass % of the entire powder. Comparative particulate water absorbing agent (8) was hence obtained.

Comparative Example 10

The same procedures were taken as in example 23 except that particulate water absorbing agent (20) was replaced with comparative particulate water absorbing agent (1) to prepare and evaluate comparative absorbent core (1). Rewetting was 6 g. Comparative absorbent core (1) was left inside a thermo-hygrostat (compact environment tester series "SH-641" manufactured by Tabai Espec Corporation) for 7 days. The thermo-hygrostat was set up to provide an atmosphere of 70±1° C. and relative humidity 65±1%. The appearance of the absorbent core was visually evaluated. The absorbent core looked yellowish.

TABLE 1

| Manufacturing Example | Dry Powder | Chelating Agent Type | ppm |
|---|---|---|---|
| 1 | a | — | — |
| 2 | b | DTPA•3Na | 100 |

| Absorbing Example | Agent | Chelating Agent Type | ppm | Phosphorous Compound Type | ppm | ASH ppm |
|---|---|---|---|---|---|---|
| 1 | 1 | DTPA•3Na | 100 | SDP | 6200 | — |
| 2 | 2 | DTPA•3Na | 1000 | PA | 5000 | 4750 |
| 3 | 3 | DTPA•3Na | 100 | SDP | 6200 | 4750 |
| 4 | 4 | DTPA•3Na | 100 | SDP | 6200 | — |
| 5 | 5 | DTPA•3Na | 100 | SDP | 6200 | 4750 |
| 6 | 6 | HIDS | 100 | SDP | 6200 | — |
| 7 | 7 | HIDS | 1000 | PA | 5000 | — |
| 8 | 8 | HIDS | 100 | SDP | 6200 | 4750 |
| 9 | 9 | HIDS | 100 | SDP | 6200 | — |
| 10 | 10 | HIDS | 100 | SDP | 6200 | 4750 |
| 11 | 11 | EDTMP•5Na | 80 | PA | 5000 | 4750 |
| 12 | 12 | EDTMP•5Na | 80 | PA | 10000 | 4750 |
| 13 | 13 | EDTMP•5Na | 200 | SHP | 3000 | 4750 |
| 14 | 14 | EDTMP•5Na | 80 | SDP | 3100 | — |
| 15 | 15 | EDTMP•5Na | 200 | SDP | 3100 | — |
| 16 | 16 | EDTMP•5Na | 200 | SDP | 6200 | — |
| 17 | 17 | EDTMP•5Na | 200 | SDP | 3100 | 4750 |
| 18 | 18 | EDTMP•5Na | 200 | SDP | 3100 | 4750 |
| 19 | 19 | EDTMP•5Na | 200 | SDP | 6200 | 4750 |
| 20 | 20 | EDTMP•5Na | 200 | SDP | 6200 | 4750 |
| 21 | 21 | EDTMP•5Na | 200 | SDP | 3500 | 3400 |
| 22 | 22 | EDTMP•5Na | 200 | SDP | 6200 | 4750 |

| Comparative Example | Comparative Absorbing Agent | Chelating Agent Type | ppm | Phosphorous Compound Type | ppm | ASH ppm |
|---|---|---|---|---|---|---|
| 1 | 1 | — | — | SHP | 2000 | — |
| 2 | — | EDTMP•5Na | 10000 | — | — | — |
| 3 | 2 | EDTMP•5Na | 200 | — | — | 4750 |
| 4 | 3 | — | — | PA | 50000 | — |
| 5 | 4 | — | — | — | — | — |
| 6 | 5 | — | — | — | — | 4750 |
| 7 | 6 | DTPA•3Na | 100 | — | — | 4750 |
| 8 | 7 | — | — | PA | 50000 | 4750 |
| 9 | 8 | — | — | SHP | 10000 | — |

ASH: Aluminum Sulfate
PA: Phosphoric Acid
SDP: Sodium Dihydrogenphosphate (Monobasic Sodium Phosphate)

TABLE 2

| Manufacturing Example | Dry Powder | GVs g/g | pH-Extr. % | Residual Monomer ppm | GEX | Initial Coloring L | a | b | AAP 4.9 kPa (g/g) | SFC ($cm^3 \cdot sec \cdot 10^{-7} \cdot g^{-1}$) |
|---|---|---|---|---|---|---|---|---|---|---|
| 1 | a | 34.0 | 6.8 | 672 | 26.6 | 91.4 | −0.4 | 4.8 | 5.0 | 0 |
| 2 | b | 32.5 | 7.7 | 650 | 24.3 | 91.1 | −0.6 | 5.3 | 6.0 | 0 |

TABLE 2-continued

| | | GVs | | Residual Monomer | | Initial Coloring | | | AAP 4.9 kPa | SFC |
|---|---|---|---|---|---|---|---|---|---|---|
| | | g/g | pH-Extr. % | ppm | GEX | L | a | b | (g/g) | (cm³·sec·10⁻⁷·g⁻¹) |
| Example | Absorbing Agent | | | | | | | | | |
| 1 | 1 | 27.5 | 7.1 | 500 | 24.2 | 89.5 | −0.3 | 5.6 | 25.4 | — |
| 2 | 2 | 26.0 | 7.5 | 450 | 23.3 | 90.1 | −0.4 | 5.2 | 24.0 | — |
| 3 | 3 | 27.2 | 7.1 | 500 | 22.5 | 90.1 | −0.4 | 5.2 | 23.5 | 102 |
| 4 | 4 | 26.7 | 7.1 | 440 | 22.3 | 90.1 | −0.1 | 6.0 | 25.0 | — |
| 5 | 5 | 26.8 | 7.1 | 450 | 22.3 | 90.1 | −0.1 | 6.0 | 23.5 | 118 |
| 6 | 6 | 28 | 8.0 | 510 | 21.6 | 89.5 | −0.3 | 5.6 | 25.0 | — |
| 7 | 7 | 26.0 | 7.5 | 450 | 21.3 | 91.0 | −0.3 | 4.4 | 24.0 | — |
| 8 | 8 | 27.7 | 7.0 | 500 | 23.0 | 90.1 | −0.4 | 6.0 | 24.0 | — |
| 9 | 9 | 27.5 | 7.1 | 510 | 22.7 | 90.1 | −0.1 | 6.0 | 25.5 | — |
| 10 | 10 | 27.6 | 7.1 | 510 | 22.8 | 90.1 | −0.1 | 6.0 | 23.5 | 96 |
| 11 | 11 | 26.6 | 6.5 | 410 | 23.3 | 90.1 | −0.4 | 5.2 | 24.0 | — |
| 12 | 12 | 26.6 | 6.5 | 410 | 23.3 | 91.0 | −0.3 | 5.2 | 24.0 | 62 |
| 13 | 13 | 26.8 | 6.1 | 400 | 24.2 | 89.4 | −0.6 | 5.9 | 24.0 | — |
| 14 | 14 | 26.8 | 6.1 | 330 | 24.2 | 89.5 | −0.3 | 5.6 | 25.0 | — |
| 15 | 15 | 28.0 | 10.1 | 410 | 19.5 | 91.0 | −0.4 | 6.2 | 25.2 | — |
| 16 | 16 | 27.6 | 10.0 | 400 | 19.4 | 90.1 | −0.1 | 6.0 | 25.0 | — |
| 17 | 17 | 26.7 | 6.1 | 330 | 24.2 | 89.0 | −0.3 | 6.0 | 23.3 | 120 |
| 18 | 18 | 26.7 | 6.1 | 330 | 24.2 | 91.5 | −0.2 | 5.9 | 24.0 | — |
| 19 | 19 | 26.7 | 6.1 | 330 | 24.2 | 89.1 | −0.5 | 7.5 | 24.2 | — |
| 20 | 20 | 27.0 | 6.1 | 330 | 24.2 | 89.0 | −0.3 | 6.3 | 23.6 | 116 |
| 21 | 21 | 27.6 | 6.1 | 330 | 24.2 | 90.2 | −0.2 | 6.0 | 23.8 | 123 |
| 22 | 22 | 27.3 | 6.1 | 330 | 24.2 | 89.2 | −0.4 | 6.5 | 23.3 | 109 |
| Comparative Example | Comparative Absorbing Agent | | | | | | | | | |
| 1 | 1 | 55.4 | 40 | 3000 | 19.6 | 90.3 | −0.3 | 4.2 | 18.0 | 0 |
| 2 | — | — | — | — | — | — | — | — | — | — |
| 3 | 2 | 27.4 | 6.1 | 330 | 24.6 | 89.6 | −0.5 | 5.9 | 22.0 | — |
| 4 | 3 | 27.2 | 15.1 | 130 | 16.3 | 90.4 | −0.6 | 6.0 | 20.0 | — |
| 5 | 4 | 27.2 | 6.5 | 510 | 23.6 | 90.5 | −0.3 | 4.8 | 25.0 | 45 |
| 6 | 5 | 27.0 | 6.0 | 510 | 24.6 | 90.7 | −0.2 | 4.7 | 24.5 | — |
| 7 | 6 | 27.4 | 6.0 | 650 | 24.8 | 90.2 | −0.7 | 6.5 | 18.0 | — |
| 8 | 7 | 27.5 | 15.0 | 130 | 16.4 | 90.6 | −0.4 | 5.7 | 23.0 | 96 |
| 9 | 8 | 27.2 | 6.7 | 500 | 23.2 | 91.6 | −0.4 | 6.8 | 20.0 | — |

TABLE 3

| | | Coloring Over Time | | |
|---|---|---|---|---|
| | | L | a | b |
| Manufacturing Example | Dry Powder | | | |
| 1 | a | 70.9 | 3.9 | 13.7 |
| 2 | b | 73.9 | 2.8 | 12.5 |
| Example | Absorbing Agent | | | |
| 1 | 1 | 79.8 | 2.2 | 9.0 |
| 2 | 2 | 80.0 | 2.6 | 10.4 |
| 3 | 3 | 79.5 | 2.6 | 10.4 |
| 4 | 4 | 79.1 | 2.2 | 10.1 |
| 5 | 5 | 79.6 | 2.6 | 10.9 |
| 6 | 6 | 80.0 | 2.4 | 10.0 |
| 7 | 7 | 79.9 | 2.4 | 12.9 |
| 8 | 8 | 79.0 | 2.6 | 11.0 |
| 9 | 9 | 78.0 | 2.2 | 11.0 |
| 10 | 10 | 79.0 | 2.6 | 12.0 |
| 11 | 11 | 80.7 | 1.9 | 8.8 |
| 12 | 12 | 82.1 | 1.7 | 8.3 |
| 13 | 13 | 78.2 | 2.4 | 9.4 |
| 14 | 14 | 79.8 | 2.2 | 8.9 |
| 15 | 15 | 85.0 | 0.5 | 7.4 |
| 16 | 16 | 85.5 | 0.5 | 7.3 |
| 17 | 17 | 80.1 | 1.9 | 8.7 |
| 18 | 18 | 80.3 | 2.0 | 8.7 |
| 19 | 19 | 81.0 | 1.1 | 8.5 |
| 20 | 20 | 81.4 | 1.8 | 8.0 |
| 21 | 21 | 83.3 | 1.6 | 7.8 |
| 22 | 22 | 81.3 | 1.8 | 8.1 |
| Comparative Example | Comparative Absorbing Agent | | | |
| 1 | 1 | 74.7 | 1.9 | 10.0 |
| 2 | — | — | — | — |
| 3 | 2 | 74.3 | 3.4 | 10.0 |
| 4 | 3 | 74.3 | 3.3 | 12.9 |
| 5 | 4 | 66.3 | 4.4 | 15.0 |
| 6 | 5 | 63.4 | 5.8 | 14.2 |
| 7 | 6 | 71.8 | 3.9 | 10.8 |
| 8 | 7 | 74.7 | 3.0 | 11.5 |
| 9 | 8 | 74.8 | 2.7 | 11.0 |

Explanation of Tables

A comparison of the water absorbing resins prepared using the same chelating agent EDTMP·5Na (200 ppm) shows that the phosphorous compounds in examples 17.18 (phosphoric acid salt 3,100 ppm) color less over time than those in comparative example 3 (no phosphoric acid salt).

A comparison shows that the phosphorous compounds and the chelating agents in examples 11 to 20 color less over time than those in comparative example 5 (no chelating agent/no phosphorous compound).

The particulate water absorbing agent of the present invention composed primarily of a polyacrylic acid- or polyacrylate-based water absorbing resin and containing a chelating agent and a phosphorous compound, including comparisons of the various examples and comparative examples, exhibits little coloring over time, especially so when a polyvalent metal (aluminum) is added, as detailed above. Furthermore, the agent has excellent absorbing properties.

The particulate water absorbing agent of the present invention, when actually used in high concentration in diapers and other like absorbing article, exhibits excellent absorbing capabilities (excellent absorbing properties under load, liquid permeability, low amount of residual monomer, excellent urine resistance (gel degradation prevention property), excellent coloring prevention) which never existed before.

The invention being thus described, it will be obvious that the same way may be varied in many ways. Such variations are not to be regarded as a departure from the spirit and scope of the invention, and all such modifications as would be obvious to one skilled in the art are intended to be included within the scope of the claims below.

INDUSTRIAL APPLICABILITY

The particulate water absorbing agent obtained by the present invention, when used in high concentration in diapers and other like thin absorbent cores, provides an absorbent core with very excellent absorbing capability, extremely excellent liquid permeability, low degree of coloring, and excellent stability in storage when compared with conventional absorbent cores.

The invention claimed is:

1. A particulate water absorbing agent, comprising 70 to 99.9 wt % of a polyacrylic acid- or polyacrylate-based water absorbing resin, 0.001 to 0.5 wt % of a water-soluble organic chelating agent, and 0.01 to 2 wt % of one or more water-soluble inorganic phosphorous compounds;
wherein the polyacrylic acid- or polyacrylate-based water absorbing resin is surface crosslinked with an organic crosslinking agent;
wherein after being exposed to a temperature of 70±1° C. and a relative humidity of 65±1% for 7 days, said particulate water absorbing agent shows an L value of 78 or greater as measured according to Hunter's Lab color system; and
wherein either:
(1) (i) the water-soluble organic chelating agent contains at least one selected from the group consisting of organic polyvalent phosphoric acids and amino polyvalent phosphoric acids and (ii) the one or more water-soluble inorganic phosphorous compounds reside locally on a surface of the polyacrylic acid- or polyacrylate-based water absorbing resin or
(2) (i) the water-soluble organic chelating agent contains at least one amino polyvalent carboxylic acid, (ii) at least one water-soluble inorganic phosphorous compound is selected from the group consisting of phosphorus acid, hypophosphorus acid, triphosphoric acid, salts thereof, and phosphate and (iii) the one or more water-soluble inorganic phosphorous compounds reside locally on a surface of the polyacrylic acid- or polyacrylate-based water absorbing resin.

2. The particulate water absorbing agent of claim 1, wherein at least one of (a) to (c) below applies:
(a) said particulate water absorbing agent contains 0 to 5 mass % particles that are 150-μm or smaller, having a mass-average particle diameter (D50) of 200 to 600 μm, and exhibiting a particle size distribution having a logarithmic standard deviation (σζ) of 0.20 to 0.40;
(b) said particulate water absorbing agent has an absorption capacity against pressure (AAP) for a 0.90 mass % aqueous solution of sodium chloride under 1.9 kPa or 4.9 kPa for 60 minutes of at least 20 (g/g); and
(c) said particulate water absorbing agent has a 0.69 mass % saline flow conductivity (SFC) of at least 5 ($cm^3 \cdot sec \cdot 10^{-7} \cdot g^{-1}$).

3. The particulate water absorbing agent of claim 1, wherein the water-soluble organic chelating agent is contained inside the water absorbing resin.

4. The particulate water absorbing agent of claim 1, comprising 0.001 to 5 wt % polyvalent metal salt.

5. The particulate water absorbing agent of claim 1, comprising 0.0001 to 3 mass ppm iron content (expressed in terms of $Fe_2O_3$).

6. A urine, faeces, or blood absorbing article, comprising the particulate water absorbing agent of claim 1.

7. A particulate water absorbing agent, comprising 70 to 99.9 wt % of a polyacrylic acid- or polyacrylate-based water absorbing resin, 0.001 to 0.5 wt % of a water-soluble organic chelating agent, and 0.01 to 2 wt % of one or more water-soluble inorganic phosphorous compounds;
wherein the polyacrylic acid- or polyacrylate-based water absorbing resin is surface crosslinked with an organic crosslinking agent;
wherein after being exposed to a temperature of 70±1° C. and a relative humidity of 65±1% for 7 days, said particulate water absorbing agent shows an L value of 78 or greater as measured according to Hunter's Lab color system; and
wherein (i) the water-soluble organic chelating agent contains at least one amino polyvalent carboxylic acid, (ii) at least one water-soluble inorganic phosphorous compound is selected from the group consisting of phosphorus acid, hypophosphorus acid, triphosphoric acid, salts thereof, and phosphate and (iii) the one or more water-soluble inorganic phosphorous compounds reside locally on a surface of the polyacrylic acid- or polyacrylate-based water absorbing resin.

8. A particulate water absorbing agent, comprising 70 to 99.9 wt % of a polyacrylic acid-or polyacrylate-based water absorbing resin, 0.001 to 0.5 wt % of a water—soluble organic chelating agent, and 0.01 to 2 wt % of one or more water-soluble inorganic phosphorous compounds;
wherein the polyacrylic acid- or polyacrylate-based water absorbing resin is surface crosslinked with an organic crosslinking agent;
wherein after being exposed to a temperature of 70±1° C. and a relative humidity of 65±1% for 7 days, said particulate water absorbing agent shows an L value of 78 or greater as measured according to Hunter's Lab color system; and
wherein (i) the water-soluble organic chelating agent contains at least one selected from the group consisting of organic polyvalent phosphoric acids and amino polyvalent phosphoric acids, (ii) at least one water-soluble inorganic phosphorous compound is selected from the group consisting of sodium dihydrogenphosphate, potassium dihydrogenphosphate, and ammonium dihydrogenphosphate and (iii) the one or more water-soluble inorganic phosphorous compounds reside locally on a surface of the polyacrylic acid- or polyacrylate-based water absorbing resin.

9. A method of manufacturing a particulate water absorbing agent, comprising the steps of:
   polymerizing an aqueous solution of a monomer composed primarily of an acrylic acid or acrylate;
   drying a water-containing gel-like crosslinked polymer obtained by the polymerizing step;
   surface crosslinking a dry powder obtained in the drying step with an organic surface crosslinking agent; and
   adding a polyvalent metal salt after the surface crosslinking step; said method further comprising the steps of:
   adding a water-soluble organic chelating agent in the polymerization or to the aqueous solution of a monomer being polymerized; and
   adding one or more water-soluble inorganic phosphorous compounds selected from the group consisting of phosphoric acid, sodium dihydrogenphosphate, potassium dihydrogenphosphate, and ammonium dihydrogenphosphate after the drying step but before the step of adding the polyvalent metal salt.

10. The method of manufacturing of claim 9, further comprising the step of adding a surfactant.

* * * * *